(12) United States Patent
Guiles et al.

(10) Patent No.: US 10,070,886 B2
(45) Date of Patent: Sep. 11, 2018

(54) METHOD OF HARVESTING TISSUE USING SEQUENTIAL SECTIONS OF A TWO DIMENSIONAL ARRAY OF NEEDLES

(71) Applicant: Medline Industries, Inc., Northfield, IL (US)

(72) Inventors: Marvin A. Guiles, Stow, MA (US); Denis Labombard, Georgetown, MA (US); Charles Sidoti, Boston, MA (US); Sameer Sabir, Arlington, MA (US)

(73) Assignee: MEDLINE INDUSTRIES, INC., Northfield, IL (US)

( * ) Notice: Subject to any disclaimer, the term of this patent is extended or adjusted under 35 U.S.C. 154(b) by 0 days.

(21) Appl. No.: 14/958,305

(22) Filed: Dec. 3, 2015

(65) Prior Publication Data

US 2016/0310158 A1 Oct. 27, 2016

Related U.S. Application Data

(60) Provisional application No. 62/151,209, filed on Apr. 22, 2015.

(51) Int. Cl.
*A61B 17/3205* (2006.01)
*A61B 17/322* (2006.01)
(Continued)

(52) U.S. Cl.
CPC .... *A61B 17/32053* (2013.01); *A61B 10/0233* (2013.01); *A61B 17/322* (2013.01);
(Continued)

(58) Field of Classification Search
CPC ............ A61B 10/0233; A61B 10/0241; A61B 10/025; A61B 2010/0258; A61B 17/322;
(Continued)

(56) References Cited

U.S. PATENT DOCUMENTS 2,426,535 A 8/1947 Turkel
3,598,108 A 8/1971 Jamshidi et al.
(Continued)

FOREIGN PATENT DOCUMENTS

DE 287651 A5 3/1991
JP 57-163208 U 10/1982
(Continued)

OTHER PUBLICATIONS http://www.dictionary.com/browse/sequential, retrieved Apr. 1, 2017.*
(Continued)

*Primary Examiner* — David C Eastwood
(74) *Attorney, Agent, or Firm* — Wilmer Cutler Pickering Hale and Dorr LLP

(57) ABSTRACT

In one aspect, the present disclosure relates to a method for harvesting biological tissue. In some embodiments, the method includes providing a device having a plurality of segments of hollow tubes, each hollow tube having at least one point at the distal end of the hollow tube, the plurality of segments forming a two dimensional array of hollow tubes, wherein each segment can include a plurality of hollow tubes; positioning the two dimensional array of hollow tubes proximal to an upper surface of a biological tissue; advancing a first segment of the two dimensional array of hollow tubes into the biological tissue to sever portions of the biological tissue from the surrounding tissue; raising the first segment of the two dimensional array of hollow tubes such that the biological tissue remains in each of the hollow tubes of the first segment; advancing a second segment of the two dimensional array of hollow tubes into the biological tissue to sever portions of the biological tissue from the surrounding tissue; and raising the second segment of the two dimensional array of hollow tubes such that the
(Continued)

biological tissue remains in each of the hollow tubes of the second segment.

14 Claims, 23 Drawing Sheets

(51) Int. Cl.
*A61B 10/02* (2006.01)
*B21G 1/08* (2006.01)
*A61B 50/30* (2016.01)
A61B 17/32 (2006.01)
A61B 17/00 (2006.01)
A61B 90/00 (2016.01)
A61B 50/00 (2016.01)

(52) U.S. Cl.
CPC .......... *A61B 17/3205* (2013.01); *A61B 50/30* (2016.02); *B21G 1/08* (2013.01); *A61B 2017/0023* (2013.01); *A61B 2017/00367* (2013.01); *A61B 2017/00477* (2013.01); *A61B 2017/00526* (2013.01); *A61B 2017/00969* (2013.01); *A61B 2017/3225* (2013.01); *A61B 2017/320064* (2013.01); *A61B 2050/0065* (2016.02); *A61B 2090/0807* (2016.02)

(58) Field of Classification Search
CPC .......... A61B 17/3205; A61B 17/32053; A61B 17/34; A61B 2017/00969; A61B 2017/320064; A61B 2017/3225; A61B 2017/00752; A61B 2017/00367; A61B 2017/3411
See application file for complete search history.

(56) References Cited

U.S. PATENT DOCUMENTS

| | | | |
|---|---|---|---|
| 3,788,320 | A | 1/1974 | Dye |
| 4,403,617 | A | 9/1983 | Tretinyak |
| 4,458,678 | A | 7/1984 | Yannas et al. |
| 4,604,346 | A | 8/1986 | Bell et al. |
| 4,640,296 | A | 2/1987 | Schnepp-Pesch et al. |
| 5,152,763 | A | 10/1992 | Johnson |
| 5,331,972 | A | 7/1994 | Wadhwani et al. |
| 5,415,182 | A | 5/1995 | Chin et al. |
| 5,439,475 | A | 8/1995 | Bennett |
| 5,611,810 | A | 3/1997 | Arnold et al. |
| 5,639,654 | A | 6/1997 | Bernard et al. |
| 5,792,169 | A | 8/1998 | Markman |
| 5,827,297 | A | 10/1998 | Boudjema |
| 5,885,226 | A | 3/1999 | Rubinstein et al. |
| 5,928,162 | A | 7/1999 | Giurtino et al. |
| 6,027,512 | A | 2/2000 | Bridges |
| 6,059,807 | A | 5/2000 | Boudjema |
| 6,440,086 | B1 | 8/2002 | Hohenberg |
| 7,651,507 | B2 | 1/2010 | Mishra et al. |
| 7,926,401 | B2 | 4/2011 | Mishra et al. |
| 8,226,664 | B2 | 7/2012 | Drews et al. |
| 8,696,686 | B2 | 4/2014 | Drews et al. |
| 9,017,343 | B2 | 4/2015 | Westerling, Jr. et al. |
| 9,060,803 | B2 | 6/2015 | Anderson et al. |
| 9,084,465 | B2 | 7/2015 | Oostman, Jr. et al. |
| 9,119,945 | B2 | 9/2015 | Simons et al. |
| 2001/0053888 | A1* | 12/2001 | Athanasiou ........ A61B 10/0233 604/154 |
| 2002/0045859 | A1* | 4/2002 | Gartstein ........... A45D 26/0004 604/117 |
| 2002/0087182 | A1* | 7/2002 | Trautman ............. A61B 5/1411 606/186 |
| 2002/0103500 | A1* | 8/2002 | Gildenberg ...... A61B 17/32053 606/187 |
| 2002/0188245 | A1* | 12/2002 | Martin ................ A61B 17/205 604/46 |
| 2003/0069548 | A1* | 4/2003 | Connelly .......... A61M 37/0015 604/264 |
| 2003/0181936 | A1* | 9/2003 | Trautman ............. A61B 17/205 606/186 |
| 2003/0195625 | A1 | 10/2003 | Garcia Castro et al. |
| 2004/0002723 | A1 | 1/2004 | Ball |
| 2004/0054410 | A1 | 3/2004 | Barrows |
| 2005/0143713 | A1 | 6/2005 | Delmore et al. |
| 2005/0226856 | A1 | 10/2005 | Ahlfors |
| 2005/0256534 | A1* | 11/2005 | Alden .................. A61B 5/1411 606/182 |
| 2005/0283141 | A1* | 12/2005 | Giovannoli .......... A61B 18/203 606/9 |
| 2006/0216781 | A1* | 9/2006 | Gebing ................... G01N 1/36 435/40.52 |
| 2007/0038181 | A1* | 2/2007 | Melamud ........... A61B 17/3478 604/158 |
| 2007/0038236 | A1 | 2/2007 | Cohen |
| 2007/0106306 | A1 | 5/2007 | Bodduluri et al. |
| 2007/0123890 | A1* | 5/2007 | Way ............... A61B 17/320016 606/79 |
| 2007/0142722 | A1 | 6/2007 | Chang |
| 2007/0142744 | A1 | 6/2007 | Provencher |
| 2007/0270710 | A1 | 11/2007 | Frass et al. |
| 2008/0045861 | A1 | 2/2008 | Miller et al. |
| 2008/0208146 | A1 | 8/2008 | Brandwein et al. |
| 2009/0146068 | A1 | 6/2009 | Agarwal |
| 2009/0198336 | A1 | 8/2009 | Qiao et al. |
| 2010/0041938 | A1 | 2/2010 | Stoianovici et al. |
| 2011/0313429 | A1* | 12/2011 | Anderson .......... A61B 10/0233 606/131 |
| 2011/0319920 | A1* | 12/2011 | Kikkawa ............. A61B 5/1411 606/186 |
| 2012/0041430 | A1* | 2/2012 | Anderson ........ A61B 17/32053 606/13 |
| 2012/0041451 | A1* | 2/2012 | Bodduluri ........ A61B 17/32053 606/133 |
| 2012/0271320 | A1 | 10/2012 | Hall et al. |
| 2012/0289985 | A1* | 11/2012 | Motai ................ A61B 10/0233 606/185 |
| 2014/0081251 | A1* | 3/2014 | Giovannoli .......... A61B 18/203 606/9 |
| 2014/0200484 | A1 | 7/2014 | Austen et al. |
| 2015/0238214 | A1 | 8/2015 | Anderson et al. |
| 2015/0250493 | A1* | 9/2015 | Umar ............... A61B 17/32053 606/133 |
| 2015/0258319 | A1 | 9/2015 | Simmers |
| 2015/0320990 | A1 | 11/2015 | Burton et al. |
| 2016/0082241 | A1 | 3/2016 | Burton et al. |
| 2016/0121091 | A1 | 5/2016 | Burton et al. |
| 2016/0136406 | A1 | 5/2016 | Berry et al. |

FOREIGN PATENT DOCUMENTS

| | | |
|---|---|---|
| JP | 07-100140 | 4/1995 |
| JP | 10-000210 | 1/1998 |
| JP | 2000139929 A | 5/2000 |
| JP | 2002505605 A | 2/2002 |
| JP | 2008036393 A | 2/2008 |
| JP | 2009509671 A | 3/2009 |
| TW | 402497 B | 8/2000 |
| WO | WO-1995/28896 A1 | 11/1995 |
| WO | WO-2005/013830 A1 | 2/2005 |
| WO | WO-2005/109799 A2 | 11/2005 |
| WO | WO-2007/041267 A2 | 4/2007 |
| WO | WO-2008/0033873 A2 | 3/2008 |
| WO | WO-2009/146068 A1 | 12/2009 |
| WO | WO-2011/140497 A2 | 11/2011 |
| WO | WO-2014/028626 A1 | 2/2014 |

OTHER PUBLICATIONS http://www.dictionary.com/browse/segment, retrieved Apr. 1, 2017.*
Moore, J. Z. et al., "Modeling of the Plane Needle Cutting Edge Rake and Inclination Angles for Biopsy," Journal of Manufacturing

(56) References Cited

OTHER PUBLICATIONS

Science and Engineering, vol. 132, pp. 051005-1-051005-8 (Oct. 2010).

* cited by examiner $$\frac{(x-h)^2}{a^2} + \frac{(y-k)^2}{b^2} = 1$$

$a$ = horizontal "radius"
$b$ = vertical "radius"
$c$ = distance from center to focus
Horizontal (pictured): $a^2 = b^2 + c^2$
Vertical: $b^2 = a^2 + c^2$

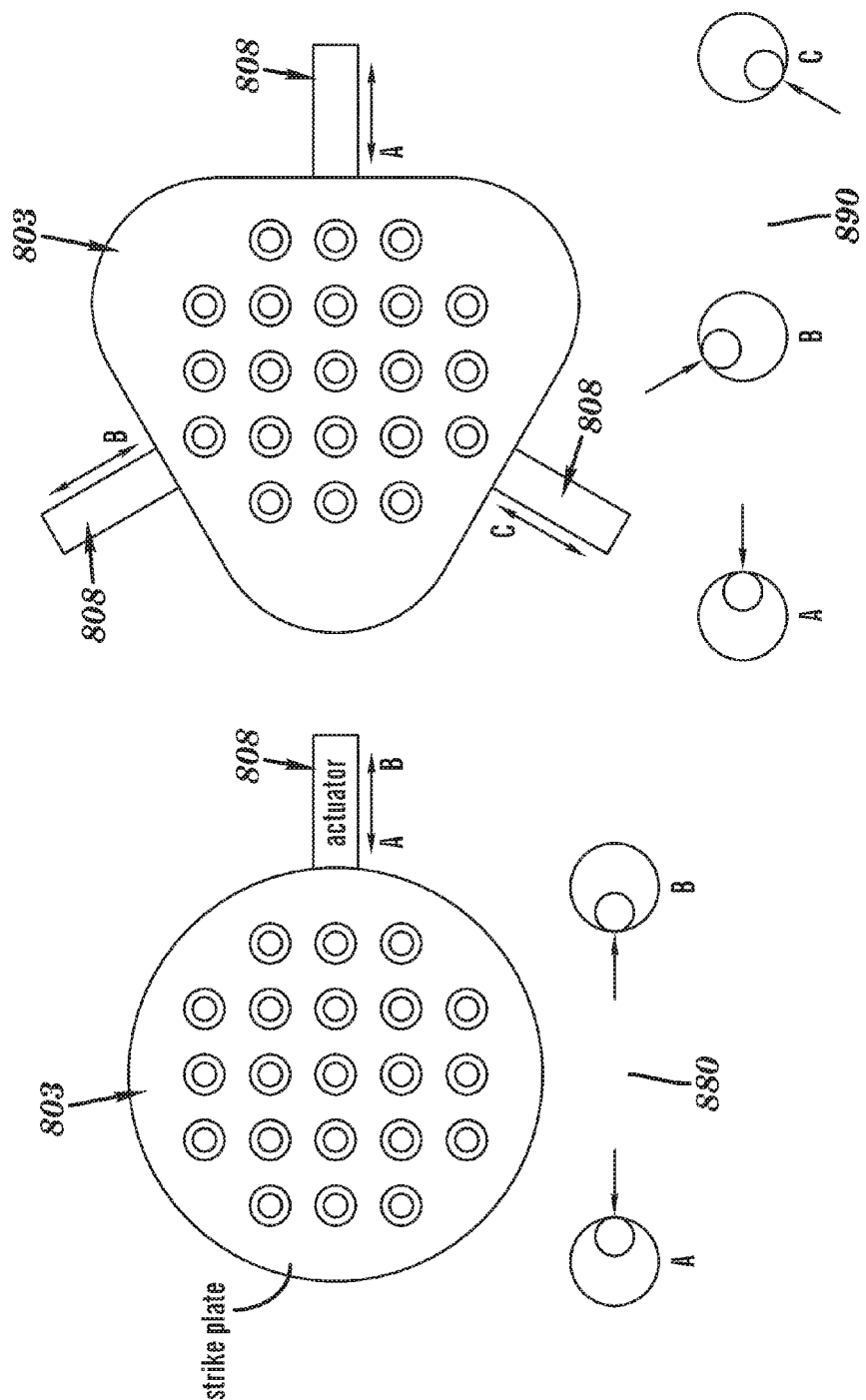

METHOD OF HARVESTING TISSUE USING SEQUENTIAL SECTIONS OF A TWO DIMENSIONAL ARRAY OF NEEDLES

RELATED APPLICATIONS

This application claims priority to U.S. Provisional Application Ser. No. 62/151,209, titled MULTIPLE-POINT CORING NEEDLE WITH NARROW HEELS, filed on Apr. 22, 2015, the entire contents of which are incorporated by reference herein.

This application is also related to the following applications, filed Dec. 3, 2015, and hereby incorporated by reference:

"METHOD AND SYSTEM FOR HARVESTING BIOLOGICAL TISSUE" (U.S. application Ser. No. 14/957, 846); and "TWO-DIMENSIONAL NEEDLE ARRAY DEVICE AND METHOD OF USE" (U.S. application Ser. No. 14/958,322).

FIELD

Embodiments of the apparati and methods described herein generally relate to a device for harvesting and depositing tissue.

BACKGROUND

Hollow implements, including needles, tubes, cannulas, or the like, may be used to core or otherwise remove skin or other tissue from a site on the body. This tissue may be used for a variety of purposes, in some cases as a graft that can be transplanted from one site (e.g., a donor site) to another site (e.g., a recipient site).

The greater the force required to insert the tube into the tissue site, the greater the possibility of damaging the tissue removed from the site and the donor site itself. In cases where it is desirable to maintain the integrity or viability of the tissue, or to otherwise facilitate removal of the tissue while applying lower force to the donor site, for example in cases where multiple tubes are applied to the tissue site at the same time, it may be advantageous to use a tube that reduces the force required to insert the tube into the tissue site. Conventional hollow tubes, such as needles, attempt to reduce the force required for insertion into the tissue site in various ways. For example, needles may include a single or double beveled ends. Double beveled needles may include two sharp points and two elliptical heels, one on either side of the needle. Alternatively, needles with zero, one, or more points may be rotated to core tissue, or needles may be formed from a low friction material, or may be coated at least in part with a lubricant. However, the tubes associated with these known techniques may apply a high amount of force on the skin when inserting the tube to remove the tissue.

The creation of 1D, 2D, or 3D arrays using currently available hypodermic needles involves the positioning or placement of individual needles—that is, at some point in the process wherein an array is to be formed, each individual needle must be handled and positioned. Such handling and positioning requires substantial labor, which, in turn, is costly in time and money.

BRIEF DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of the invention.

FIGS. 8A-8H depict apparati for the vibratory actuation of a needle, according to embodiments of the present disclosure.

SUMMARY

Figure 1A:
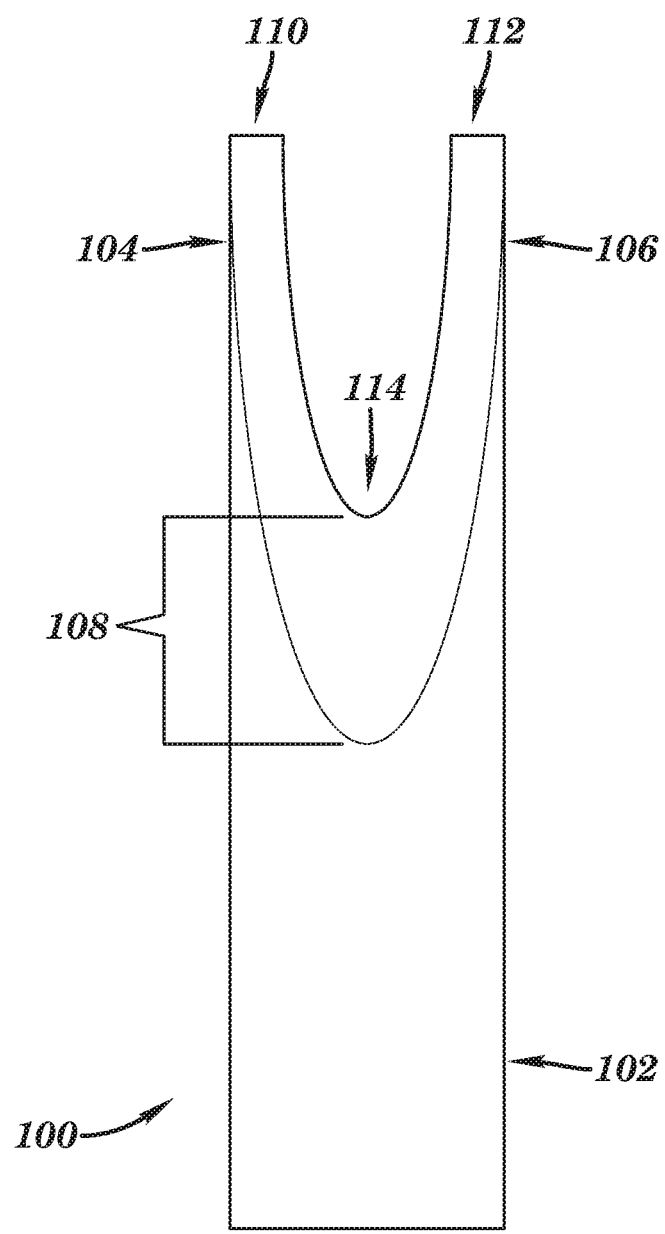
FIG. 1A is a side view of a double bevel needle.

In one aspect, the present disclosure relates to a method for harvesting biological tissue. In some embodiments, the method includes providing a device having a plurality of segments of hollow tubes, each hollow tube having at least one point at the distal end of the hollow tube, the plurality of segments forming a two dimensional array of hollow tubes, wherein each segment can include a plurality of hollow tubes; positioning the two dimensional array of hollow tubes proximal to an upper surface of a biological tissue; advancing a first segment of the two dimensional array of hollow tubes into the biological tissue to sever portions of the biological tissue from the surrounding tissue; raising the first segment of the two dimensional array of hollow tubes such that the biological tissue remains in each of the hollow tubes of the first segment; advancing a second segment of the two dimensional array of hollow tubes into the biological tissue to sever portions of the biological tissue from the surrounding tissue; and raising the second segment of the two dimensional array of hollow tubes such that the biological tissue remains in each of the hollow tubes of the second segment.

In some embodiments, the first segment can include a row of hollow tubes. In some embodiments, the first segment can include a plurality of rows of hollow tubes. In some embodiments, the first segment can be a portion of a row of hollow tubes. In some embodiments, the first segment can be a plurality of portions of rows of hollow tubes. In some embodiments, each hollow tube can have an inner diameter less than about 1 mm. In some embodiments, each hollow tube can have an inner diameter less than about 0.8 mm. In some embodiments, a plurality of pins are provided, each of the pins located within a central lumen of each of the hollow tubes. In some embodiments, the method can include positioning the two dimensional array of hollow tubes over a wound site; scattering the biological tissue within each of the hollow tubes of the first segment over the wound; scattering the biological tissue within each of the hollow tubes of the second segment over the wound. In some embodiments, the scattering of the first segment and the second segment can occur at the same time. In some embodiments, the scattering of the first segment and the second segment can occur at different times. In some embodiments, the biological tissue can include skin tissue and adipose tissue. In some embodiments, the advancing of first and second segments can occur at the same time. In some embodiments, the advancing of first and second segments can occur at different times. In some embodiments, the raising of the first and second segments can occur at the same time. In some embodiments, the raising of the first and second segments can occur at different times. In some embodiments, advancing can include firing a solenoid. In some embodiments, the two dimensional array can include a circle. In some embodiments, the circle can include an area of about one square inch. In some embodiments, the device can have about 300 hollow tubes.

DESCRIPTION

The present disclosure relates to a device and method for extracting micro-sized columns of skin tissue from a donor site and depositing and/or scattering the harvested tissue onto a wound. The deposited tissue promotes healing of the wound site. The device can harvest from approximately one square inch of donor site by using several hundred needles. In some embodiments, the needles used to harvest the tissue can have narrow heels to provide easier insertion into the donor site. In some embodiments, the needles can be manufactured using a stamp and roll method, while in other embodiments, the needles can be manufactured using an accordion method. In other embodiments, each individual needle can be sharpened and cut and assembled into arrays. In some embodiments, all the needles can be inserted into the donor site simultaneously, while in other embodiments, selected groups of needles can be inserted sequentially. In some embodiments, the needles can be vibrated upon entry into the donor site and/or inserting the harvested tissue into the wound. In some embodiments, the needles can be rotated while inserting into the donor site.

Multiple-Point Coring Needle With Narrow Heels

FIG. 1A is a side view of a double bevel needle 100. Needle 100 can be a cylinder or tube 102 and can include one or more points, for example, two points 104 and 106, that may be formed by grinding or cutting the needle at an angle on both sides relative to the longitudinal axis of the tube 102 to form a bevel 108. Hollow tube 102 can be formed of metal or any other structurally rigid material. Bevel 108 forms what is referred to herein as an elliptical heel 114. A heel is defined as the section of the needle where the tangent of the cutting edge is −45 to −90 degrees, and +45 to +90 degrees from the axis of the needle. A single bevel needle can have one side with a bevel. A double bevel needle can have one bevel on one side of the needle and a second bevel on the opposite side of the needle. The angle of the bevel that forms tips of the needle may vary, but in one example the angle is about 30 degrees, although other larger or smaller angles may be used. For example, the angle could be in the range of about 10-35 degrees. Needle points 104 and 106 can each have a flat cutting edge, 110, 112 with a length equal to the thickness of the wall of tube 102. In this embodiment, when the needle is inserted into tissue, sharp points 104, 106 can enter the tissue with a relatively low force due to the sharpness of points 104, 106 of needle 102, but elliptical heels 114, which are formed where the proximal portions of the two points converge in the needle body, may result in higher insertion forces, due to the blunt angle at which they contact and enter the tissue. In cases where multiple needles are applied to the tissue at the same time, for example as a needle array, the force required to insert the array may be increased relative to the number of needles in the array and could significantly inhibit a user from inserting the array at a tissue site or cause significant pain upon insertion. In cases where it is desirable to maintain the integrity or viability of the tissue, the additional force required to insert the heel of the needle may damage the tissue at the donor site as well as the tissue that is removed.

Figure 1B:
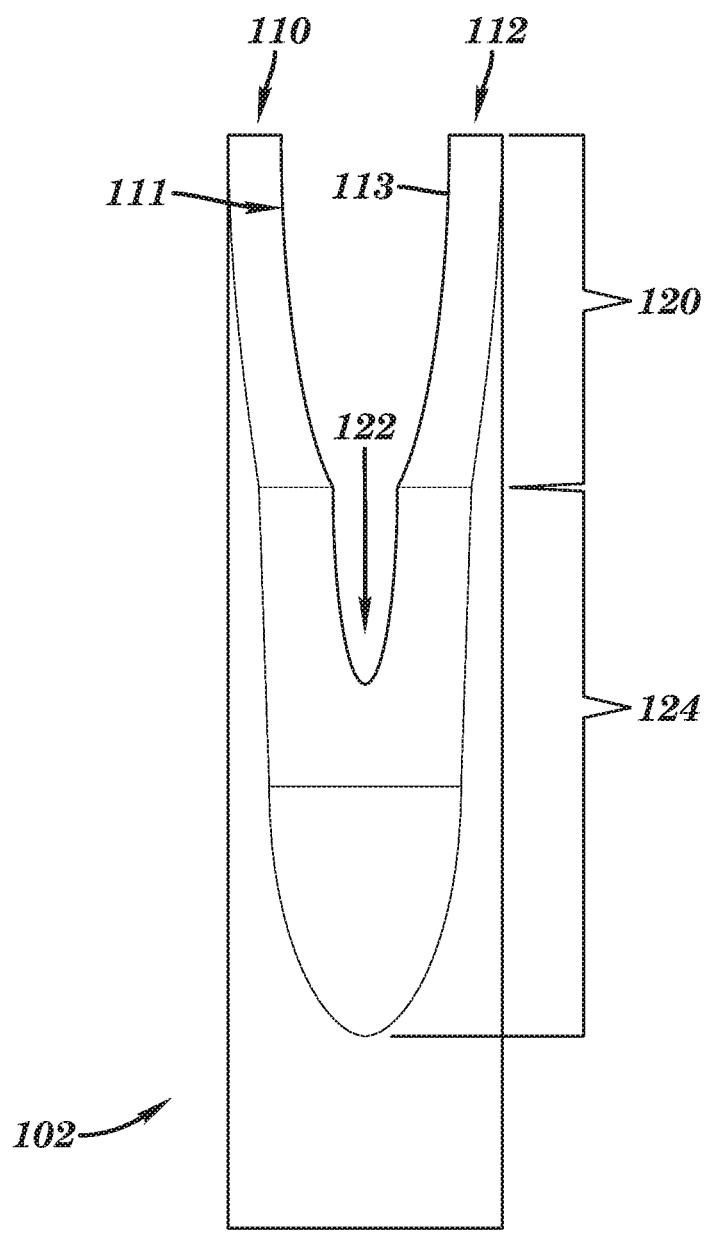
FIG. 1B is a side view of a double bevel needle, according to aspects of the present disclosure.
Figure 1C:
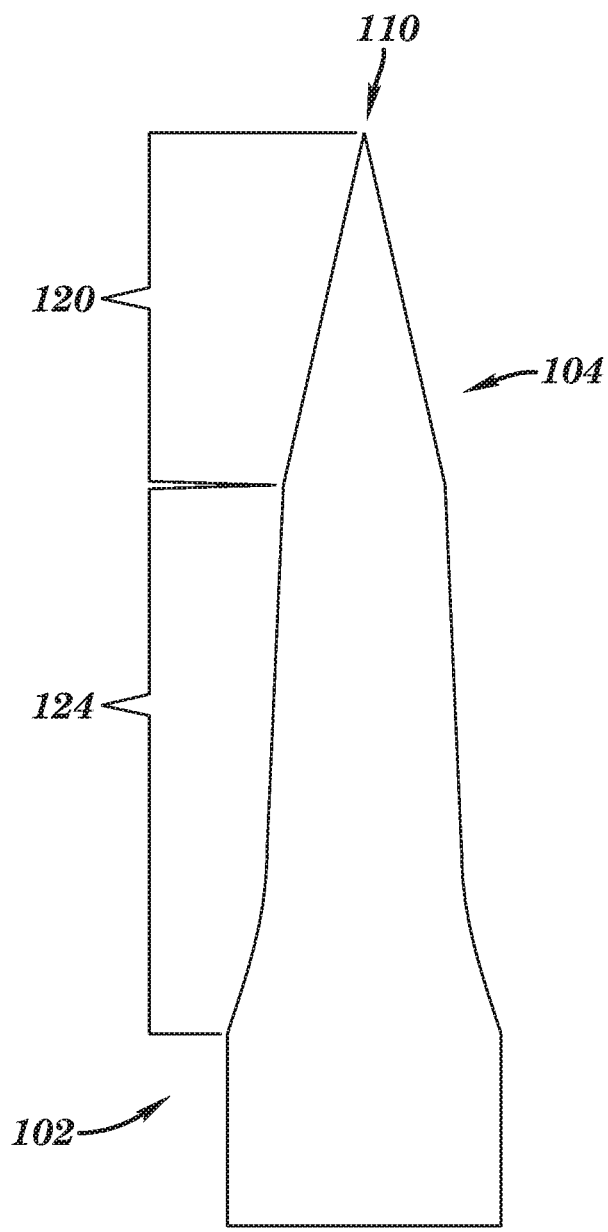
FIG. 1C is a side view of the double bevel needle of FIG. 1B, rotated ninety degrees, according to aspects of the present disclosure.

FIG. 1B is a side view of a double bevel needle, according to aspects of the present disclosure. FIG. 1C is a side view of the double bevel needle of FIG. 1B, rotated ninety degrees, according to aspects of the present disclosure. This needle differs from the needle shown in FIG. 1A in that it has two bevels on each side of the needle, for a total of four bevels on the needle. The use of two bevels on each side results in a significantly narrower heel 122. The narrower heel 122 can provide a sharper cutting edge than prior art needles, thus causing less tissue damage and pain upon insertion of the needle into the donor site. According to embodiments of the present disclosure, a cutting edge of the described needles starts at one of the needle tips and runs back toward the heel 122, continues through heel 122, and back up to the other tip. In order to harvest tissue with the least impact to the surrounding tissue and least pain to the patient, the cutting edge should be sharp. Sharp, as used herein, means that the tube material comes to as fine a point as possible all along the cutting edge. For example, a tip whose cutting edge is either a single point, or is a line that is shorter than the wall thickness of the tube. Further, as used herein, narrow refers to the width of the heel, while sharp refers to the width of the cutting edge, e.g., the sharpness of a knife edge. Narrow is defined as the width of the heel being approximately 15% or 10% or less of the inside diameter of the cannula or needle. While the present disclosure describes a needle with two bevels per side to create each heel, the disclosed narrow heel could be achieved with more than two bevels or with a curved bevel. The disclosed embodiments achieve a narrow heel while not requiring an excessive distance between the heel and the tip. Accordingly, the bevel angle, where it crosses the internal diameter of the tube should be as shallow as reasonably possible. In some embodiments reasonably possible refers to an acceptable length from the heel to the tip. A shallower angle will provide a narrower heel, but will also create a longer distance from heel to tip. The intended use of the needle can determine the acceptable length. For skin harvesting, that distance can be kept under about 2 mm.

Figure 1D:
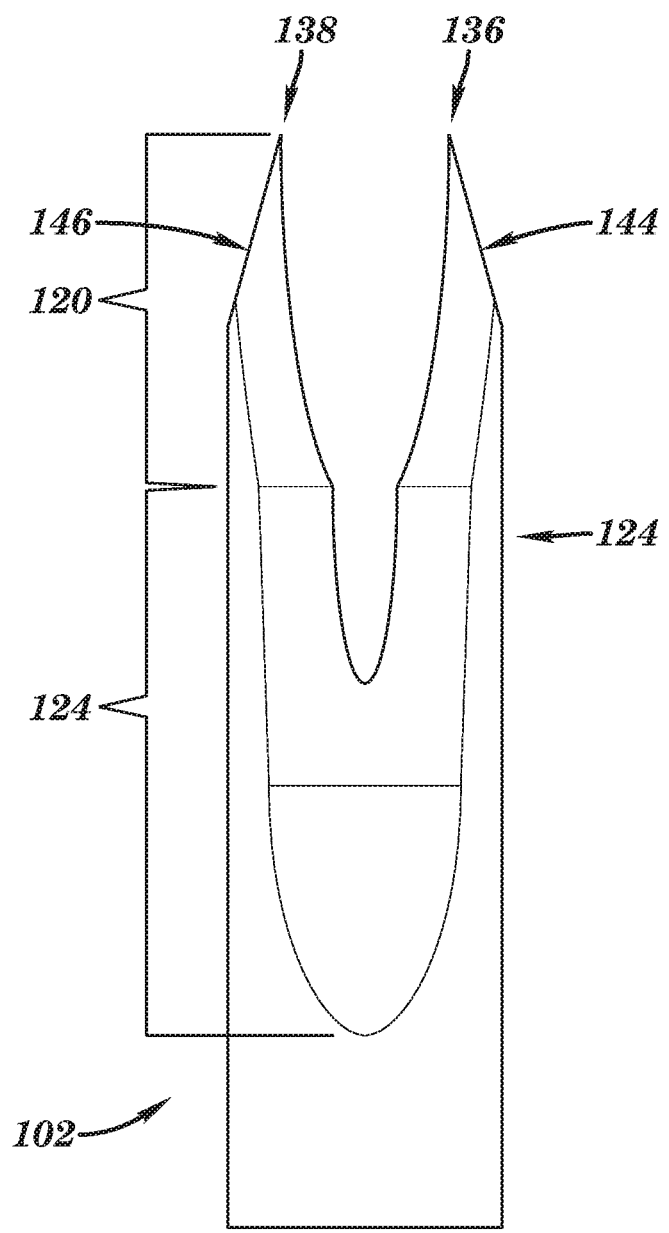
FIG. 1D is a side view of another embodiment of a double bevel needle, according to aspects of the present disclosure.
Figure 1E:
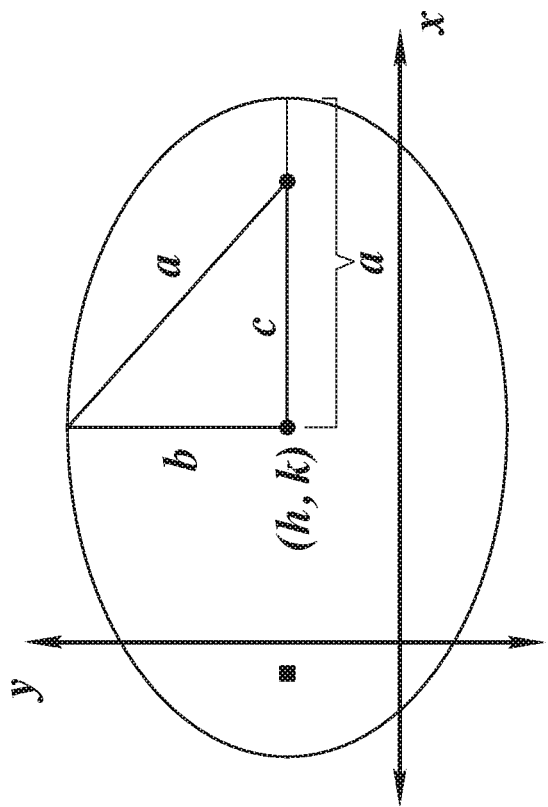
FIG. 1E shows an ellipse and equation for an ellipse.

With reference to the equation of ellipse shown in FIG. 1E, to achieve a "narrow" heel, the present disclosure seeks to make c (the distance from the center to one of the foci of the ellipse, i.e., the bevel) as long as is reasonable without having the needle tip become too long, and have the ratio of a over c as close to 1 as is reasonably possible. This is because as the device cores, the needle is pushed into the tissue. Therefore, when the tissue is up away from the heel, the direction of travel creates a slicing effect as with a knife.

When the base of the heel is reached, the cutting edge is perpendicular to the pushing direction, which requires more force to cut through the tissue. A "narrow heel" keeps the angle made between the cutting edge and the axis of the needle less than 45 degrees as long as possible (as close to the heel as possible). This keeps the slicing effect as long as possible.

As can be seen in FIGS. 1B and 1C, a distal end of tube 102 can be shaped to form points 110, 112. As shown in FIG. 1C, a first bevel 124 and a second bevel 120 are formed on the front and back of the distal end of tube 102. Second bevel 120 forms tips 110, 112, or points of the needle. First bevel 124 in conjunction with second bevel 120 forms narrow heel 122.

With continued reference to FIG. 1C, to form first bevel 120, the front and back sides of the distal end of tube 102 can each be ground or cut at an angle relative to the axis of the tube 102, e.g., to form a beveled structure at the distal end of tube 102. For example, an exemplary tip angle is about 30 degrees as shown in FIG. 1C corresponds to an angle relative to the axis of the tube, α, of about 15 degrees. Though angle α in this example is about 15 degrees, angle α may be larger or smaller than 15 degrees. For example, angle α may range from about 10 degrees to about 18 degrees.

The second bevel angle 124 on each side of tube 102 is generally shallower than first bevel 120, and forms sharpened heel 122 shown in FIG. 1B. The angle of second bevel 124 relative to the longitudinal axis of tube 102, can be 6 degrees and can create a tight, narrow ellipse that approximates a point at the heel 122 on each side of the needle as seen in the front view in FIG. 1B.

In one embodiment, second bevel 124 can be formed by grinding or cutting the front and back sides at the distal end of the tube 102 at an angle β relative to the axis of tube 102. The second angle β is shallower than the first angle α to form a narrow ellipse that approximates a point at the heel 122 of the needle tip. Though second angle β in this example is about 6 degrees, angle β may vary, so long as second angle β is shallower than first angle α. In alternative embodiments, the needle may be formed with more than two bevel angles. For example, three or more bevel angles may be formed on each side of the tube, with the degree of the bevel decreasing, the further the bevel is from the distal end of the tube. In further alternative embodiments, the two or more angles may be formed on each side of the tube by way of forming a curved surface on each side of the tube where the angle of the curve varies along the length of the tube. In some embodiments, the narrow heel can be achieved with only one bevel per needle side. However, the singular bevel would need to be a shallow angle up to the tip of the needle, which may greatly increase the distance from heel to tip of the bevel.

With continued reference to FIGS. 1B and 1C tube 102 has two tips 110, 112 that can be formed by grinding opposite sides of tube 102 at a first bevel angle α relative to the long axis of the tube 102. The two tips 110, 112 have inner cutting edges 111, 113 that converge at a point, or nearly a point 122 at the heel of the needle tip. Inner cutting edges 111, 113 are formed from the inner wall surface of the tube, which is exposed by first bevel 120. A tube with two tips 110, 112 will have four inner cutting edges, two associated with each point. Though the cutting edges 111, 113 on the front of tube 126 are shown in FIG. 1B, corresponding cutting edges on the back of tube 102 are not shown. In some embodiments, the inner cutting edges may be further sharpened by applying an additional bevel to the inner or outer wall surface of the tube, or to both the inner and outer wall surfaces. Further sharpening the inner wall edges enables the tube to pass through tissue with a lower force slicing motion. The narrow point at heel 122 is formed from the shallow second bevel 124 described with reference to FIG. 1C. By narrowing cutting edges 111, 113 to a point or nearly a point at heel 122, the cutting edge of the needle can continue slicing the tissue as the needle is inserted and the force required to insert the needle into the tissue is decreased compared to double bevel needles without a sharpened heel. Unlike FIG. 1A, where heel 114 is curved, and the vertex is almost parallel to the flat distal ends of tips 110, 112, in the embodiments shown in FIGS. 1B-D, only a small section of the cutting edge, at the vertex of the ellipse, is pushed perpendicularly into the tissue. By minimizing the area of the vertex and forming it with an angle, the force required to insert the tube into tissue is lowered, and the tube is able to slice tissue with inner cutting edges 111, 113 along their length as the tube is inserted into tissue.

FIG. 1D is a side view of another embodiment of a double bevel needle, according to aspects of the present disclosure. As further shown in FIG. 1D, a third bevel 144 and a fourth bevel 146 can be optionally provided in a direction orthogonal to the first and second bevels 120, 124. These additional bevels are characterized by the angle λ which represents the angle at which each of the opposing lateral sides of the tube 102 can be ground or cut relative to the longitudinal axis of tube 102. In the exemplary embodiment, angle λ can be about 6 degrees but it may be larger or smaller, for example between about 3 and about 9 degrees. These bevels 144, 146 can be provided to reduce the size or width of the sharp edge of the tips 136, 138 formed at the end of the tube 102 to further facilitate insertion of the tube 102 into a donor-site tissue. The depth of bevel may vary. For example, bevel may be shallow, leaving a flat cutting edge at points 136, 138, or bevel may be deeper such that the tips form sharp points as shown in FIG. 1D. The angle of bevel may vary as well. The points or extensions 136, 138 formed from angle λ that form a narrow angle at their tip as shown in FIG. 1D can be inserted into the tissue using a smaller force as compared to points formed from an angle larger than λ, although this force may be applied for a longer distance and/or time to achieve full insertion of the tube 102 into the tissue than that used for tips formed from a larger angel λ thus have a shorter length of the angled tip region.

Though the exemplary embodiment shown in FIGS. 1B-1D discloses a tube with two points and two heels, further embodiments may include tubes with any number of points and heels greater than one. For example, in a further exemplary embodiment, a tube can be provided with three points or extensions provided at a distal end thereof. This exemplary configuration can be formed, e.g., by grinding three portions of the tube at a first angle α relative to the long axis thereof, where the three portions can be spaced apart by about 120 degrees around the perimeter of the tube. In still further exemplary embodiments, a tube can be provided that includes more than three points or extensions provided at a distal end thereof, e.g., a tube having four, five, six, seven, eight, or more points. In this configuration, one or more of the heels may be formed with a second shallower angle relative to first angle α to form one or more sharpened heels as described in the present disclosure. The second angle may be different for each heel on the tube. The initial force needed for the tube to penetrate the tissue can be approximately proportional to the number of points if the angle of each point or extension is held constant. Providing a greater number of points extensions at the distal end of the tube can improve mechanical stability of the tube and/or geometrical control of the severed tissue, but it may use a larger force to penetrate the tissue. However, if the needle points are sharper because the angles are lower, a system with a greater number of needle points can actually have lower overall force than existing systems with fewer, duller needle points.

The various geometries and points described herein can be used in any of the exemplary embodiments of the present disclosure, e.g., for the various devices and methods described herein. For example, the hollow tube can be provided with a bevel angle α of less than about 15 degrees, e.g., about 12 degrees. Such an acute tip angle can provide sharp tips of the points or extensions that can more easily penetrate a biological tissue or matrix material. A narrower tip angle α, e.g. about 6 degrees, may be preferable for harvesting and/or inserting micrografts in a denser or tougher tissue or matrix material, where the narrower tips of the points or extensions can be configured to more easily cut through the tissue or matrix material when the tube is inserted therein. A secondary bevel having an angle λ, such as the exemplary tips of the points or extensions shown in FIG. 1D, can further facilitate insertion of the distal end of the tube into various materials by providing the tips of the points or extensions that are smaller and more pointed. However, the tips of the points or extensions that are sharper and/or narrower, e.g., those having small tip angle α and/or a secondary bevel with angle λ, can also be more prone to wear, bending, or other deformation, if the tube is repeatedly inserted into tissue or a matrix. Accordingly, the tip geometry selected for a particular application can be selected based on the type of material or tissue the apparatus will be used with, as well as the desired lifetime of the tube.

The inner diameter of the tube can be selected or structured to approximately correspond to a particular diameter of a tissue portion such as a micrograft to be removed from a donor site. According to one exemplary embodiment, the inner diameter of the tube can be less than about 1 mm. For example, 18 or 20 gauge biopsy needles (e.g., having an inner diameter of 0.838 mm and 0.564 mm, respectively) or the like can be used to form the tube. A biopsy tube having a larger gauge (and smaller inner diameter) can also be used. Based on the interaction between the tube, width or diameter of the harvested tissue can be slightly smaller than the inside diameter of the apparatus used to harvest it.

Living tissue can be provided with nutrients via a diffusional transport over distances of about 0.1 mm. Accordingly, tubes according to the present disclosure may be configured to extract exemplary micrografts having at least one dimension that is less than about 0.6 mm, e.g., less than about 0.3 mm or, e.g., less than about 0.2 mm, which can exhibit improved viability and likelihood to survive, and they may grow when used in a graft. Such exemplary micrografts can be better able to receive nutrients (including, e.g., oxygen) when placed in a recipient site, prior to revascularization of the tissue.

Tubes according to the present disclosure may also be configured to extract larger micrografts, e.g., those having a width of about 1-2 mm, which can also benefit from such diffusional transport of nutrients, and can also be more likely to survive than significantly larger portions of graft tissue (e.g., conventional full-thickness, split-thickness or meshed grafts). These larger sizes can be preferable for harvested tissue that is heterogeneous, e.g., tissues that may contain certain structures that can be preserved within a single micrograft. For example, skin tissue has certain structures such as hair follicles, sebaceous glands, etc., and harvesting somewhat larger micrografts from skin may help to preserve these tissue structures when harvested and transplanted. On the other hand, smaller micrografts, e.g. those less than about 0.6 mm, or about 0.2 mm wide, can be suitable for relatively homogeneous tissues, such as muscle tissue, where there are few or no larger structures in the tissue to be preserved.

In embodiments where a tube as described in the present disclosure is used to harvest micrografts, a width or diameter of the holes at the donor site produced during harvesting (which can correspond approximately to the diameters of the portions of harvested micrografts) can be less than about 2 mm, or less than about 1 mm. In certain exemplary embodiments of the present disclosure, the tube may be configured to extract a micrograft having a diameter or width of less than about 0.6 mm, less than about 0.3 mm, or about 0.2 mm. The size of the exemplary holes at the donor site can be selected, e.g., based on the effects of creating small damage regions in the donor site that can heal rapidly and/or without scarring, and on creating portions of tissue that can be small enough to promote viability when transplanted or placed in a growth medium, and large enough to form a sufficient amount of graft tissue and/or capture tissue structures that may be present in the donor tissue. The advantageous sharp heel design described in the present disclosure can further minimize damage to the donor site tissue by limiting the amount of force required to insert the tube into the donor site, thereby decreasing tissue morbidity.

Other aspects of a cannula, tube or needle having the properties described herein may be realized as well. In one embodiment, the cannula may be used to harvest or extract graft tissue. In this embodiment, the cannula is configured to remove tissue from a donor site, and facilitate placement of the tissue at a recipient site. Placement of the tissue at a recipient site may be performed by inserting the cannula at the recipient site, or otherwise expelling the tissue from the cannula and depositing, placing it, or otherwise distributing the tissue at the recipient site. The recipient site may be another location on the same individual as the donor site, a different individual, or it may be another material such as a matrix. In some cases the matrix may be a biocompatible matrix, which may form a graft or larger copy of the donor tissue, such as that described in U.S. patent application Ser. No. 13/102,711, the entirety of which is incorporated herein by reference. U.S. patent application Ser. No. 12/936,173 is also incorporated by reference in its entirety.

In some embodiments, the tube may also include a collar or stop or the like provided on an inner or outer surface of the tube or may otherwise be affixed to an apparatus holding the tube such that it limits the insertion depth of the tube. In some embodiments the stop may comprise a sensor, camera or other mechanism that prevents the tube from extending past a particular depth. In one embodiment, the stop or other mechanism may be affixed to the tube at a particular distance from the ends of the tips, or this distance may be adjustable, e.g., over a range of lengths by moving the stop along the axis of the tube. In one example, a stop may be positioned on the tube to allow insertion of the tube up to the dermal/fatty layer of the skin.

In one example, the tube may be inserted into the tissue at the donor site, and the tips and cutting edges and may sever a tissue portion from the surrounding tissue as the tube penetrates the donor site tissue. The tube may be inserted to a specific depth, e.g., until a stop contacts the surface of the donor site. A portion of tissue can be present within a lower portion of the tube. Such tissue can remain within the tube, and be separated from the donor site with the tube to form a micrograft when the tube is removed from the donor site.

The exemplary micrograft thus formed can include both epidermal tissue and dermal tissue. For example, a micrograft can be removed from a donor site by removing the tube, including the micrograft, from a donor site without rotating the tube around the axis thereof and without suction. The points or extensions provided on the tube can facilitate such removal of micrograft tissue from the surrounding tissue at a donor site.

A micrograft or other tissue may be removed from the tube in a variety of ways. For example, by providing pressure through an opening at a proximal end of the tube. Such pressure can be mechanical, hydraulic, pneumatic, etc. For example, the pressure can be provided by blowing into the opening, by squeezing a flexible bulb attached to the proximal end of the tube, by opening a valve leading from a source of elevated pressure such as a small pump, etc. In other embodiments, the tissue can be removed from the tube by using the pins disposed within the tubes to push the grafts out of the tubes. Alternatively, tissue such as micrografts can be harvested by inserting the tube into a plurality of locations of a donor site. Each micrograft within the tube can then push any micrografts above it towards the proximal end of the tube, which may be open or coupled to a receptacle configured to store the micrografts for transport. Once the tube has been substantially filled with the harvested tissue, each additional insertion of the tube into the donor site can facilitate pushing of an uppermost micrograft within the tube out of the proximal end or into the receptacle or other collection device. Other mechanisms, such as vibration, may be used to remove the micrografts from the tube as well.

In embodiments where the cannula is inserted into and/or pierces the recipient site to remove the tissue, the exemplary configuration of the tube distal end, including the reduced dimensions of the heel to a point or a near point, such that the cutting surface is at an angle to the tissue for as long as possible, is advantageous to the recipient site in addition to the advantages realized at the donor site. For example, trauma is reduced at the recipient site when the cannula is inserted therein for the same reasons discussed previously with respect to the donor site.

In an alternative embodiment, the cannula may be used in conjunction with a piercing cannula. In this embodiment, the cannula may be disposed inside a piercing cannula and advanced through the piercing cannula to deposit tissue at a recipient site. The piercing cannula may also include at least one narrow heel as described in the present disclosure.

Many advantages over conventional cutting or piercing tubes or cannulas may be realized by the apparatus of the present disclosure. In one embodiment, an apparatus may be provided that includes a plurality of tubes, each having sharpened heels as described in the present disclosure. The plurality of tubes may be mechanically affixed or otherwise coupled to a base to form an array of tubes. In this configuration, multiple portions of tissue may be harvested from a donor site simultaneously, or near simultaneously, by a single insertion of the array of tubes into the donor site. The array may be formed in a number of configurations, including in linear array, or in any form of a pattern along the base. The spacing of tubes in the pattern may be regular or somewhat irregular or varied, which may both facilitate insertion of the array at the donor site and may also avoid formation of patterns at the donor site. The needle array spacing can be chosen to facilitate insertion and also, in some embodiments, to avoid collateral damages, e.g., tearing, to the surrounding tissue.

Generally, a greater number of tubes in the array corresponds to a greater force required to insert the tubes into tissue or a matrix simultaneously, which may be undesirable if the force is too large. However, when needles having the narrow heel discussed in the present disclosure are assembled into arrays of needles that are to be inserted into a donor site for the purpose of harvesting tissue, the amount of force required to insert the array into the patient is disproportionately low compared to arrays of conventional needles that do not have narrow heels. The apparatus of the present disclosure also creates a donor-site wound that is much less substantial than if performed using conventional implements, thus resulting in much less trauma at the donor site and greater patient comfort. These unexpected advantages allow for larger arrays that may have more than tens or hundreds of needles, which result in a tool that can harvest larger areas of tissue while minimizing donor site morbidity and pain to the patient. The dispersion of the needle array can reduce tissue damage and provide cleaner coring of the donor site.

Figure 2:
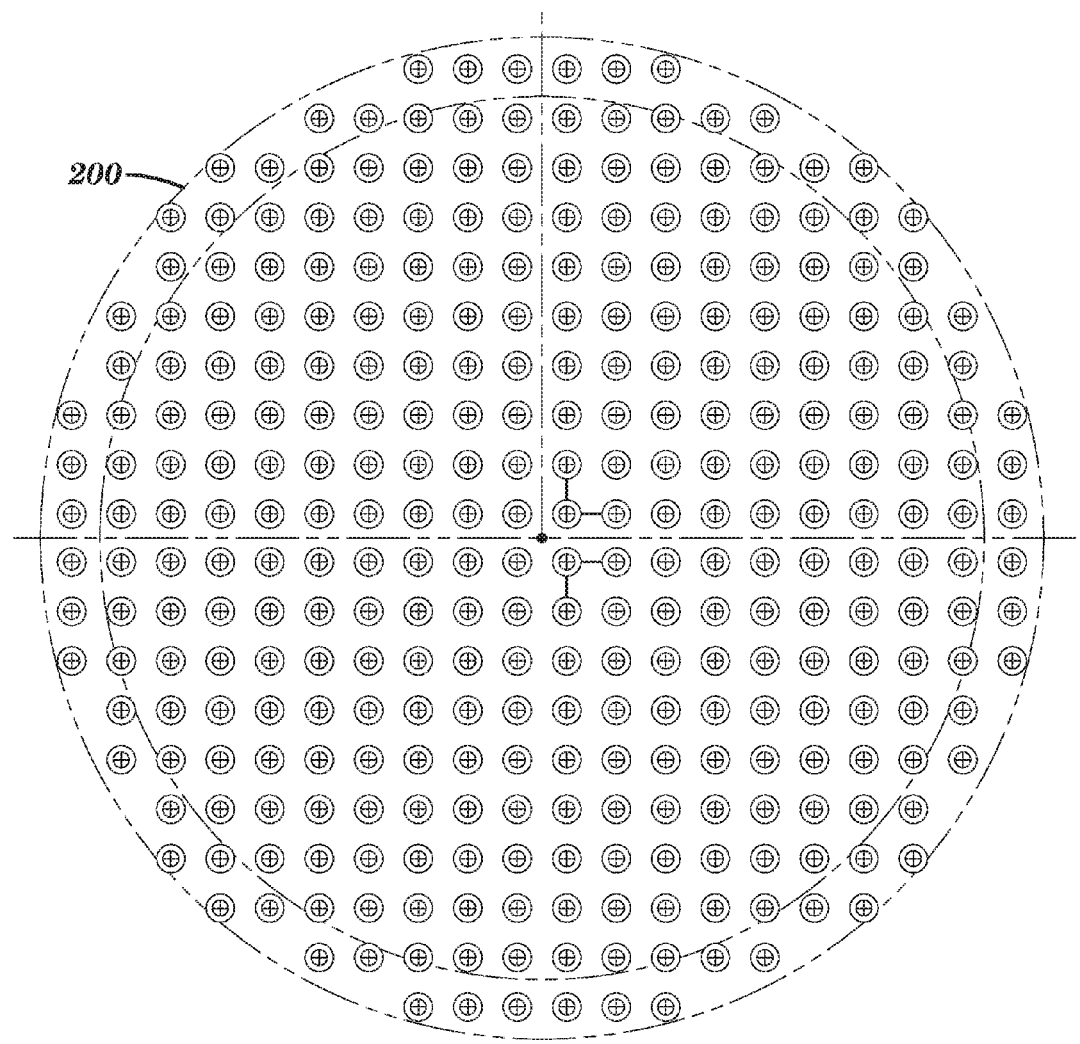
FIG. 2 is a top view of an array of needles, according to embodiments of the present disclosure.

For example, FIG. 2 is a top view of an array of needles 200, according to embodiments of the present disclosure. Array 200 is circular and contains 316 needles and has an area of approximately one square inch. In the example of FIG. 2, 21 gauge regular wall hypotube needles are used with pins having an outer diameter of approximately 0.018 inches. The needles are spaced 0.056 inches from center and the circle has a diameter of about 1.13 inches. This configuration of needles can result in a harvest corresponding to 10% area of the harvest site, that is, the total cross-sectional area of the 316 tissue columns equals 0.1 square inches, which is 10% of one inch. Needle density in the array can range from about 1% to about up to 20%, for example, 10% density.

The circular array is formed by assembling a plurality of rows of needles, either horizontal or vertical rows. This design is modular and the configuration can take on any shape or size using various size rows as modules. In some embodiments, all of the needles can be actuated, e.g., inserted into the tissue, simultaneously. In other embodiments, groups or sections of needles can be actuated sequentially. For example, the array can be divided into quadrants and each quadrant can be sequentially actuated. Sequentially can refer to actuating each row in a linear order, (e.g., row1, row2, row3), or non-linear (e.g. row1, row10, row3). Or, each row of needles can be separately and sequentially actuated. Finally, each single needle could be separately and sequentially actuated. In some embodiments, the circular array of needles can be divided in to a plurality of pie wedges, e.g., three, four, five, six or more wedges, and each wedge can be sequentially actuated. In some embodiments, two or more arrays can be actuated simultaneously and other arrays can be actuated individually or in groups until all needles are actuated. In some embodiments, one row is actuated at a time, e.g., 20 rows are individually actuated in sequence, while in other embodiments, two, three, four or more rows can be actuated at a time. An advantage to sequentially actuating segments of the array is that insertion of a segment can require less force on the donor site than insertion of the entire array, which may result in less trauma at the donor site. In some embodiments, the array is driven using a solenoid. Multiple actuations using the solenoid can sequence the insertion line by line. In some embodiments, two solenoids can be used, each solenoid firing in opposite directions to prevent kick back of the device, and further reducing force applied to the donor site and thereby reducing trauma to the surrounding tissue.

Generally, exemplary tubes may include a pin provided in the central lumen or opening of the tube. The diameter of the pin can be substantially the same as the inner diameter of the tube or slightly smaller, such that the pin can be translated along the axis of the tube while filling or occluding most or all of the inner lumen of the tube. In some embodiments, the pin can be formed of a low-friction material, or coated with a low-friction material such as, e.g., Teflon® or the like, to facilitate motion of the pin within the tube and/or inhibit accumulation or sticking of biological material to the pin. The distal end of the pin can be substantially flat to facilitate displacement of micrograft tissue within the tube when the pin is translated. In a further exemplary embodiment of the present disclosure, an apparatus can be provided with a plurality of the tubes and of the pins. All of the tubes can be translatable with respect to the pins together using a single actuator, or certain ones of the tubes can be translated simultaneously and/or sequentially using a plurality of the actuators.

In some embodiments, for harvesting tissue the needles are first inserted to full, specified depth at the location selected for harvesting. In some embodiments, the depth of insertion can be limited by the use if a hub. All of the needles can be bonded into a "hub" or "stop" (discussed above) and the hub limits the depth because when it hits the skin the penetration of the needles stops. In some embodiments, the needles can be inserted into the skin at a high speed through the use of a solenoid. In some embodiments, the needles can be inserted using a loaded spring or any other means that releases or provides a high energy impact. When the needles enter the harvest location, a skin column is formed within the hollow space of the needle. Once the needles have been inserted into the tissue to the appropriate depth and the tissue columns are present within the needles, the user removes the device from the harvesting area. The tissue columns remain in place within the needles. Then, the user transports the device, with the harvested columns to the wound site for depositing. Depositing can be achieved by either inserting the tissue columns into the wound or wound matrix, or by dropping (scattering) the tissue columns onto the surface of the wound.

For inserting, the user positions the device over the wound, and presses the needle array into the wound, wound dressing, or wound matrix. Once the needles with tissue columns are inserted, the needles are retracted, keeping the pin tips at the surface of the wound location. This holds the previously harvested tissue columns in place while the needle are retracted. Then, the device is pulled away from the wound location, and the tissue columns have been inserted at the wound site. The retraction of the needles pushes the tissue columns out of the needles. For scattering, the user positions the device over the wound, retracts the needles, and actuates the solenoid (or other actuation method) again, which causes the needle tips to extend down the length of the pins and push the tissue columns off the pins. Then the needles stop quickly and retract again, which throws the tissue columns from the tips of the needles.

The exemplary tubes of the present disclosure may be formed of any sufficiently strong material that is preferably biocompatible or inert with respect to biological tissue, e.g., a 304 stainless steel, a surgical stainless steel, etc. In some embodiments, the tube can be coated with a lubricant or low-friction material, such as Teflon®, to further facilitate the passage of the tubes through tissue. Bevels and other sharp edges may be formed by cutting, grinding, etching, photo etching, electropolishing, or the like. Further finishing processes can be applied to the tube 20, such as electropolishing, to increase sharpness of the cutting edges, or providing a ME-92® chromium coating to increase the material strength. Such finishing processes can increase the cutting effectiveness and/or improve the useful service life of the tube.

The above-described methods for harvesting and scattering tissue can be implemented using the described narrow heeled needles or any other type of harvesting apparatus, for example, needles having only one or two bevels, without a narrow heel.

Method of Manufacturing Coring Needles

The previously described needles can be manufactured via a plurality of methods, including (1) grinding individual tubes (2) a stamp and roll technique and (3) an accordion method. The latter two methods will be discussed below.

Stamp and Roll

In one embodiment, a stamp and roll method can be used to create a needle structure from a flat sheet of material. Through the stamp and roll method, 1D, 2D, and 3D arrays of needles and associated structures can be created. For purposes of this discussion, a 1D array can be defined as an arrangement of needles wherein the needle points are positioned in a line or curve in space, with equal spacing between needle points, or with a repeating pattern of variable spacing; 2D array can be defined as an arrangement of needles wherein the needle points are positioned in a plane in space, with a repeating pattern of spacing between needle points; 3D array can be defined as an arrangement of needles wherein the needle points are positioned over a three dimensional surface in space, in a repeating pattern of spacing between needle points.

Currently, hollow needles, and particularly, hypodermic needles, are fabricated from cylindrical tubing. This imposes limitations on the finished geometry of the needles based on manufacturing methods of forming hollow tubes, and structural integrity of hollow tubes. In addition, the creation of 1D, 2D, or 3D arrays using currently available hypodermic needles involves the positioning or placement of individual needles—that is, at some point in the process wherein an array is to be formed, each individual needle must be handled and positioned.

The described method permits the creation of needles of any geometry that can be conceivably derived from a flat sheet of material that is cut and folded, rolled, bent, twisted, or otherwise formed. Furthermore, the described stamp and roll design achieves arrangements of a multiplicity of such needles in a regular pattern in space, with a high degree of precision and without the requirement to handle or position individual needles.

In the electronics industry, for example, conductive connector pins are typically manufactured from flat metal ribbons using a process sometimes called "stamp and roll." Typically, the metal ribbon is paid-out from a reel, and fed continuously into a machine wherein the components are cut and formed, and the finished components are then spooled onto a take-up reel. By virtue of this manufacturing process, the finished components are spaced equally along the ribbon. Each connector pin is designed to be easily broken off of the ribbon (the unused portion of the ribbon is called the "carrier") and the loose pins are then available for incorporation into plastic connector housings The carrier, or carrying web, is a processing item that is normally discarded in standard stamp and roll processing, after the formed parts are removed from it. According to some embodiments, however, the present methods do not require the removal of the needles from the carrier. Instead the carrier can be used to hold the needles together in the array and can be an integral part of the needle array. Accordingly, in some embodiments, the carrier can automatically be part of the line of needles formed in the stamp and roll process, and can serve the same purpose as the carrier that can be added to the needles in other array forming processes.

The needles disclosed herein may be manufactured using the "stamp and roll" process, but are not limited to that process. Furthermore, note that in the device disclosed herein the carrier may be optionally (and advantageously) designed to be an integral part of the finished assembly, rather than discarded.

Figure 3:
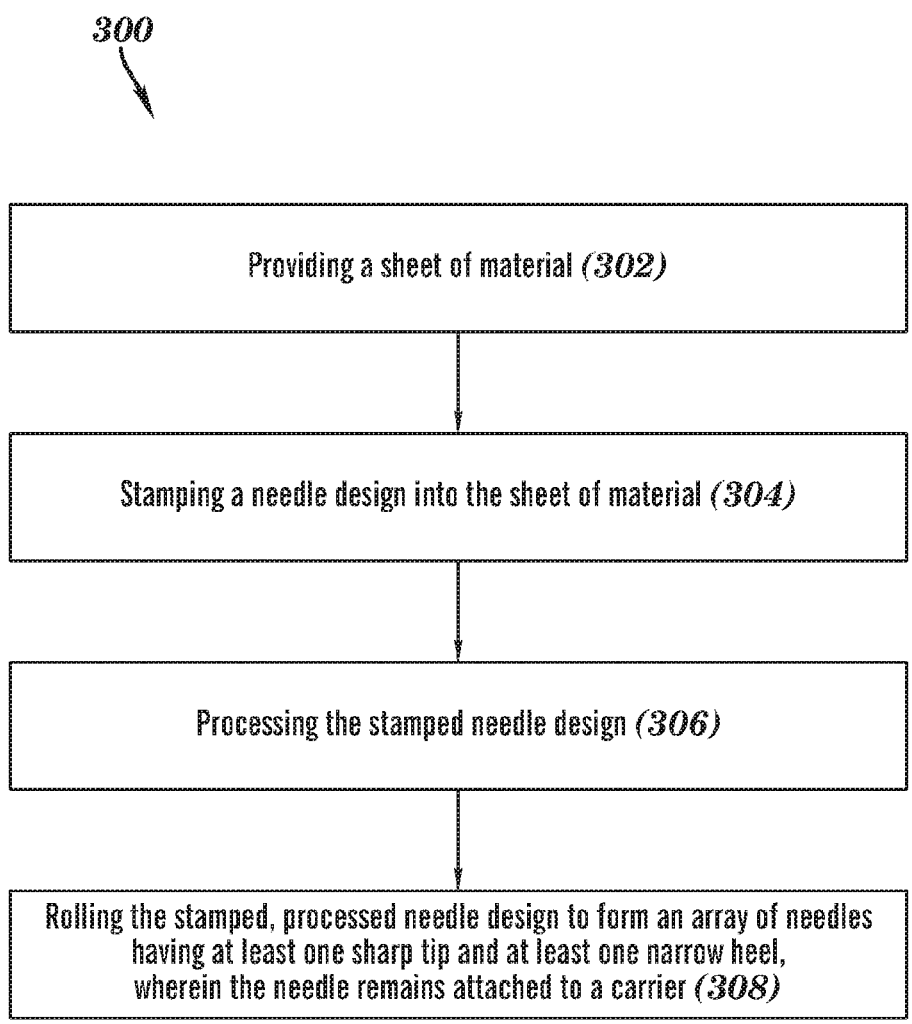
FIGS. 3 and 4 describe a stamp and roll technique for manufacturing needles, according to embodiments of the present disclosure.
Figure 4:
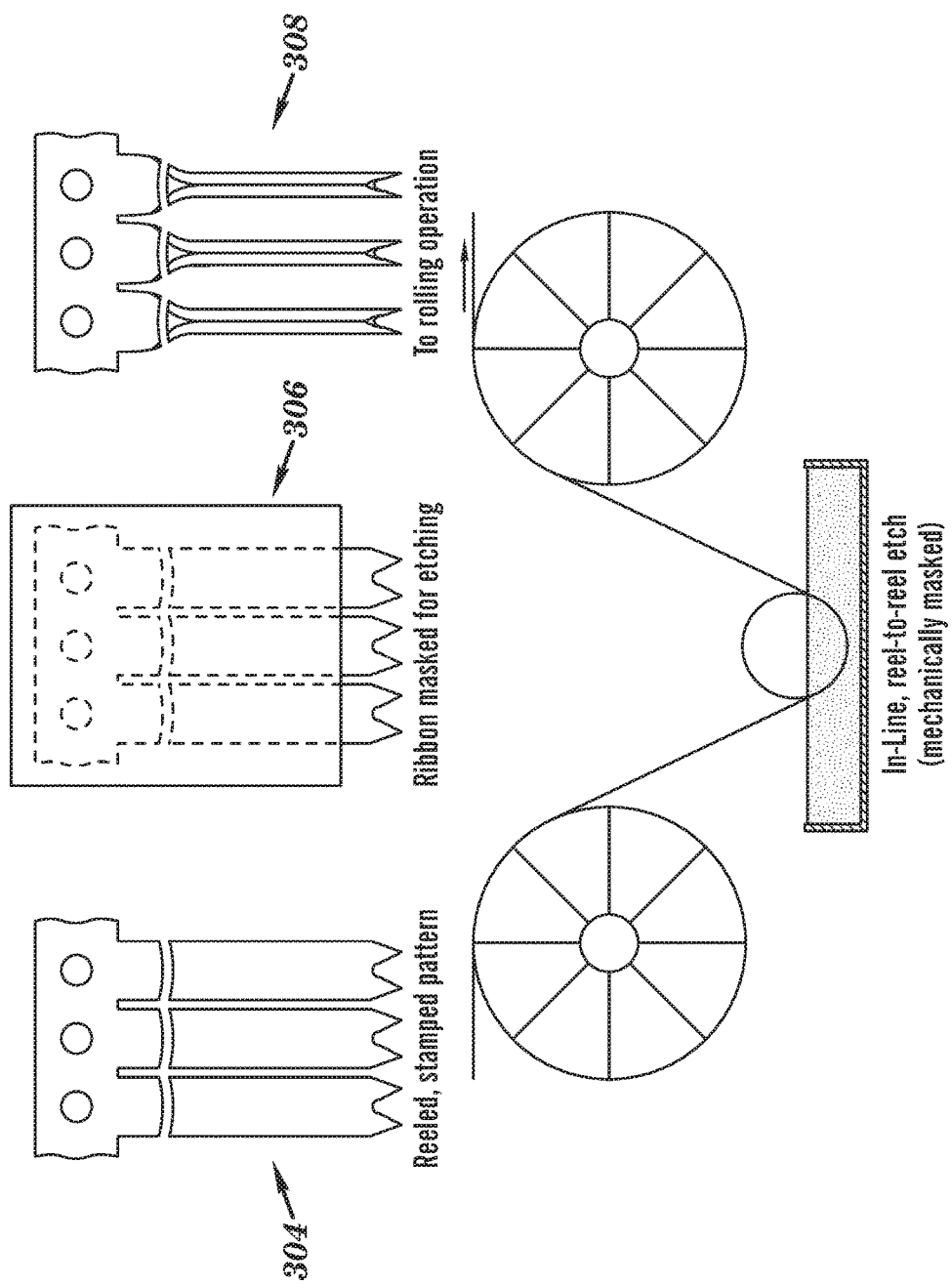

FIGS. 3 and 4 describe a stamp and roll technique for manufacturing needles, according to embodiments of the present disclosure. The disclosed stamp and roll technique can include the following steps, as illustrated in FIGS. 3 and 4:

1. providing a sheet of material; (302)—not shown in FIG. 4
2. stamping a needle design into the sheet of material, (304);
3. processing the stamped needle design; (306) and
4. rolling the stamped, processed needle design to form an array of needles having at least one sharp tip and at least one narrow heel, wherein the needle remains attached to the carrier (308).

In some embodiments, the needle design can include a plurality of needles to be formed and can include both a carrier and a needle. In some embodiments, the resulting needle can include at least one narrow heel and at least one needle tip. In some embodiments, the above method can be performed using a machine or manufacturing apparatus. The machine or other manufacturing apparatus may include a processor, software or other non-volatile memory programmed to perform the above steps.

According the stamp and roll technique, several advantages can be achieved. For example, the needle geometry can be formed from a flat sheet of metal, rather than limited by the manufacturing constraints of hollow tubes, and the stamp and roll technique also can allow for complex needle geometry. For example, in one embodiment, the design can have a flat portion of the structure at the top, an open funnel-like structure below the top, a substantially closed cylindrical structure in the middle, and a double-pointed structure at the bottom tip. Further, these techniques can allow for a multiplicity of needles to be formed with a precise spacing between needles, and the number of needles in the 1D array may be of any number. In some embodiments, a given length of the 1D array (for example, a length consisting of 20 elements) may be stacked or layered with additional given lengths to form a 2D or 3D array. The spacing between 1D portions of the 2D or 3D arrays may be controlled by placing material spacers between the layers. A further advantage is that a wide variety of geometric arrangements of neighboring layers are possible, including square lattice, triangular lattice, hexagonal lattice, etc. For example, any portion of the array may be bonded, encapsulated, or otherwise incorporated into a larger structure with the intention of imparting support, strength, orientation, or other properties to the whole.

Another advantage of the described manufacturing method is that both surfaces of the flat starting material are readily accessible prior to needle formation, permitting a wide variety of surface treatments, including coating, texturing, ribbing, anodization, etc., any or all of which may be included in the design of the inner or outer surface of the needle. Further, all edges of the needle are accessible prior to needle formation, permitting a wide variety of edge contours (e.g. single and multiple needle points; abutting, overlapping, interlocking, scalloped seams, helical seams, etc.) and a wide variety of edge treatments, including coined, beveled, serrated, sharpened, deburred, electro-polished, etc.

In some embodiments, a given length of the 1D array may be further bent or formed, for example back onto itself to form a layered 2D or 3D array. For example, a given length of the 1D array may be further bent or formed, for example into a circle, with the needle points oriented radially, or into a circle with the needle points oriented orthogonal to the plane of the circle, or, in general, along any curve in space. So that, in principle, any 3D surface may be populated with needle points. In some embodiments, the stamp and roll method can create a single point, a double point, or a triple point needle. The resulting needle can have any number of points desired and stamped into the sheet before rolling. In some embodiments, the needle does not have a point at all.

In some embodiments, the 1D needle array may be subjected to secondary processes (for example immersive or spray coatings, chemical sharpening, welding or secondary closure of seams, etc.) as a unitary structure, permitting parallel processing of a multiplicity of elements. As described herein, the stamp and roll technique allows for the formation of extremely narrow heels because there are no tubular geometry restrictions. Because this technique does not involve sectioning a cylinder, it does not limit the heel to being an ellipse; for example, the heel may be formed into an angular shape. Accordingly, the narrowness of the heel of a needle made according to these techniques is only limited to how narrow it be made while sharpening a flat sheet before forming the needle. For example, a heel can be made in the shape of a point, instead of a radiused heel, by forming the heel with the seam of the needle.

Further advantages of the described stamp and roll method include precise, repeatable, and low-cost means of forming complex needle geometries. The various needle geometries can include single or multiple points of virtually any shape. The described methods can create non-cylindrical cross-sections, e.g., a square or any other geometrical shape, flared tops (for easy insertion into the needle bodies, for example insertion of an obturator) and other unusual or difficult geometries. The disclosed method also can provide for textured inside and outside surfaces of the needles.

Pick and Place Accordion Method of Manufacturing

Another method for manufacturing needles and needle arrays can include a pick and place accordion method. This method can be used to create 1D, 2D, and 3D arrays of needles and associated structures. According to these methods, needles or their precursor materials are handled in groups comprised of more than one needle, where said handling may include, but is not limited to, positioning, stacking, mounting, and fixturing. In some embodiments, these methods can be performed using a machine or other manufacturing apparatus. Through use of this method, the spacing between needles may be efficiently, accurately, and precisely established. In some embodiments, the spacing may be regular or patterned, and can extend over 1D, 2D, or 3D space.

The accordion tubes used in this manufacturing method can be manufactured using various conventional wire-forming processes, such as is used for springs and other complex wire-like structures. These processes include automated versions which typically consist of (1) pinch-rollers which provide a mechanism for the continuous feed of raw material, and (2) computer numerical control ("CNC") bending and forming tools, which permit the manipulation and shaping of the continuous length of raw material. The disclosed accordion method can use an automated wire-forming process that is augmented as described in this disclosure, but is not limited to that process.

According to aspects of this method, needles or their precursor materials are processed in groups of more than one needle. As used herein, processing may include but is not limited to grinding, welding, brazing, deburring, sharpening, texturing, and polishing. Groups of needles may be ganged or stacked to form larger groups or arrays, said larger groups also, optionally, possessing accurate and precise inter-needle spacing.

Figure 5A:
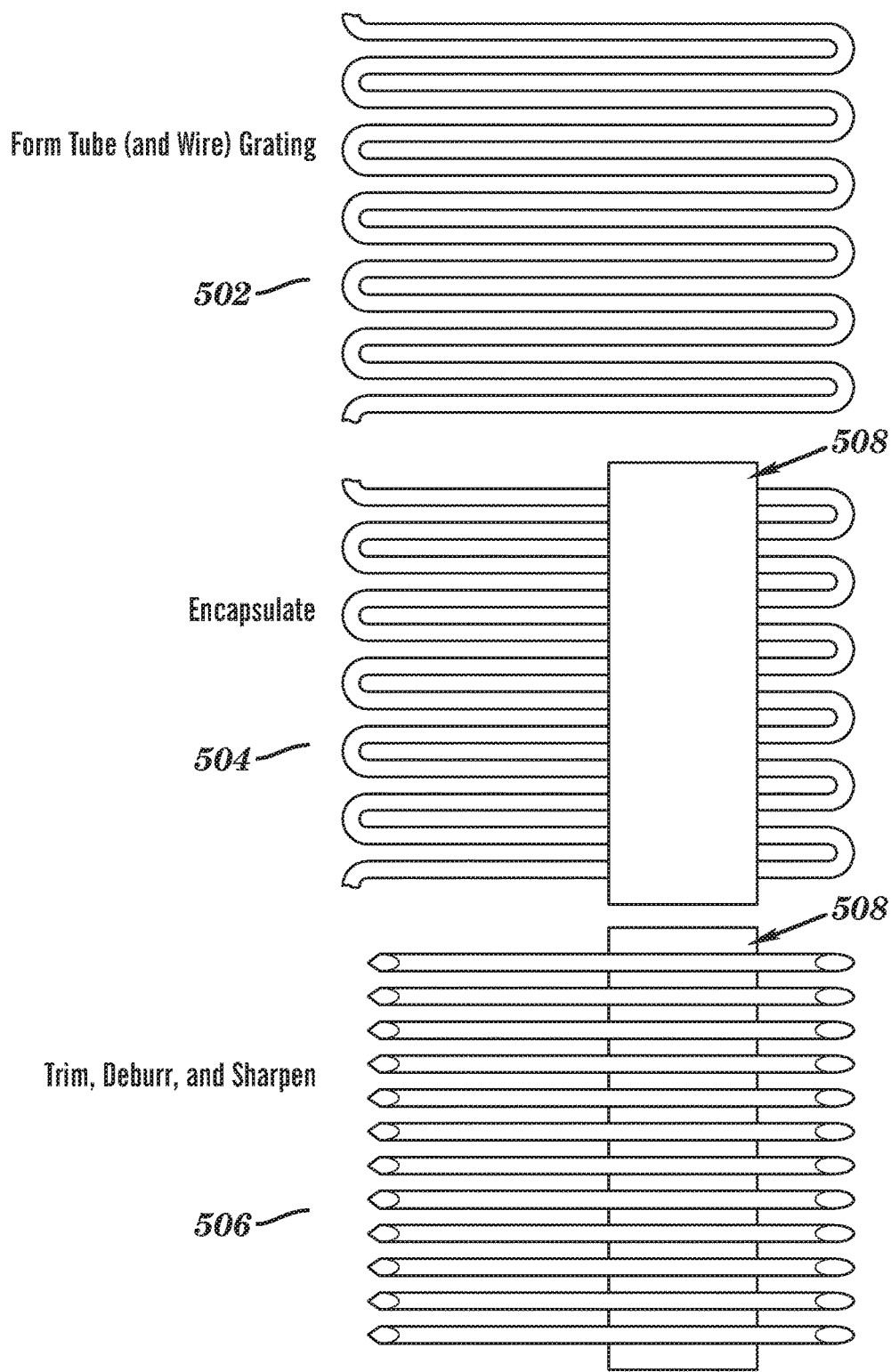
FIG. 5A depicts a pick and place accordion method for manufacturing needles, according to aspects of the present disclosure.
Figure 5B:
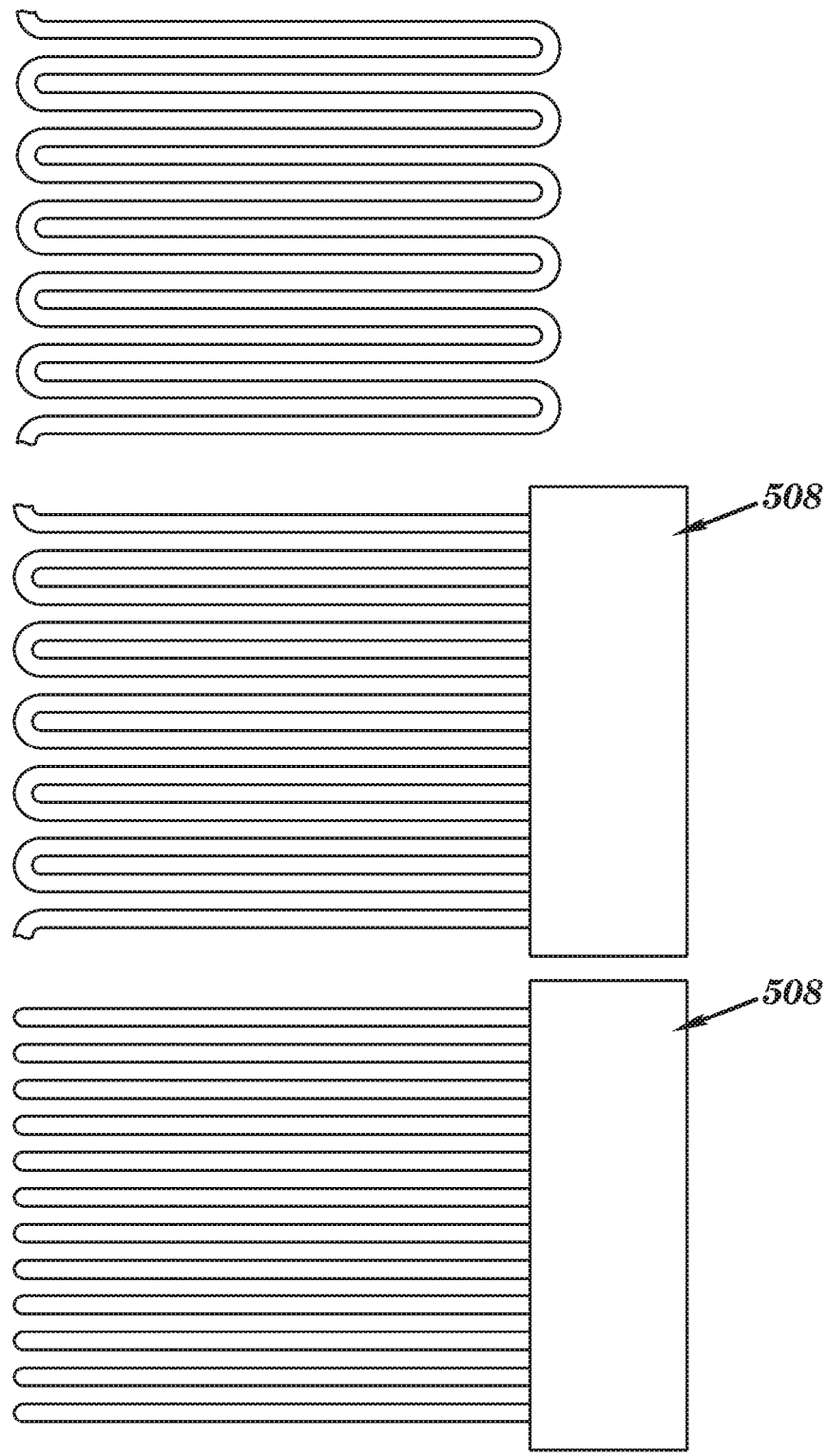
FIG. 5B depicts a pick and place accordion method for manufacturing pin arrays, according to aspects of the present disclosure.

FIGS. 5A and 5B depict a pick and place accordion method for manufacturing needles, according to aspects of the present disclosure. In some embodiments, a length of tubing is folded or bent into an accordion shape, as shown at 502 in FIGS. 5A and 5B. The number of bends may range from a single bend to many. The cross-sectional integrity and the straightness of the folded tubing is maintained within a "critical zone" that lies between the bends. For example, at the bends of the accordion shape, the cross section of the tube will deform and not be round. As needles should be round if round pins are used, in some embodiments, the straight sections can be long enough that the bends, and any deformed sections close to the bends are removed, leaving enough material for an appropriate needle length.

The bend radii of the folded shape are such as to facilitate insertion of the piece into a needle array spacer or carrier 508, as shown at 504. In some embodiments, the bend radii can be about one half the desired center-to-center spacing of the needles, for example, about 0.056 inches. In some embodiments, the carrier can be composed of stainless steel. In other embodiments, the carrier can be made from a plastic material. Many different clamping arrangements may be employed to temporarily secure the folded shape in carrier 508. In some embodiments, as shown in FIG. 5A, carrier 508 is affixed to the tubing in a location that does not encompass an end portion of the tubing. In FIG. 5B, carrier 508 can be affixed to one end of the tubing. The folded shape may be tightly held by carrier 508 (for example, by mechanical means such as by an interference fit with the grooves, or by a snap action into the grooves) or it may be permanently secured to the carrier 508 in a variety of ways, including welding, bonding, insert-molding and brazing.

In some embodiments, the carrier can include registration holes. Registration holes are holes in the carrier such that the carrier can be attached to other carriers or to something else. In some embodiments, the registration holes can be used to stack lines of needles to make different shapes. In some embodiments, the thickness of the carrier can be important because the spacing between lines of needles can be made farther or closer when multiple carriers are stacked. Other means of registration, for example, shoulders, pins, etc., are possible as well. The carrier is designed to impart the desired spacing between neighboring tubular sections, both within the grouping (by means of the center-to-center spacing of the grooves of the carrier) and between groupings (by means of the registration holes, and the thickness, length, and, width of the carrier).

Once a single folded shape (or, optionally, several shapes) is/are secured within one or more carriers, the folded shape is processed, as shown at 506. Examples of processing can include but are not limited to cutting, grinding, sharpening, beveling, texturing, polishing, deburring, shaping, bonding, and welding. In some embodiments, the single folded shape, or multiple shapes, can be processed to form an array or sub-array of needles, with a precise inter-needle spacing and in a precise geometric relation with respect to the carrier.

During processing, the sub-assembly, comprising the single folded shape (or multiple folded shapes) and the carrier, along with other fixturing components, is processed as a unitary structure, permitting parallel processing of a multiplicity of needle elements.

Figures 6A, 6B:
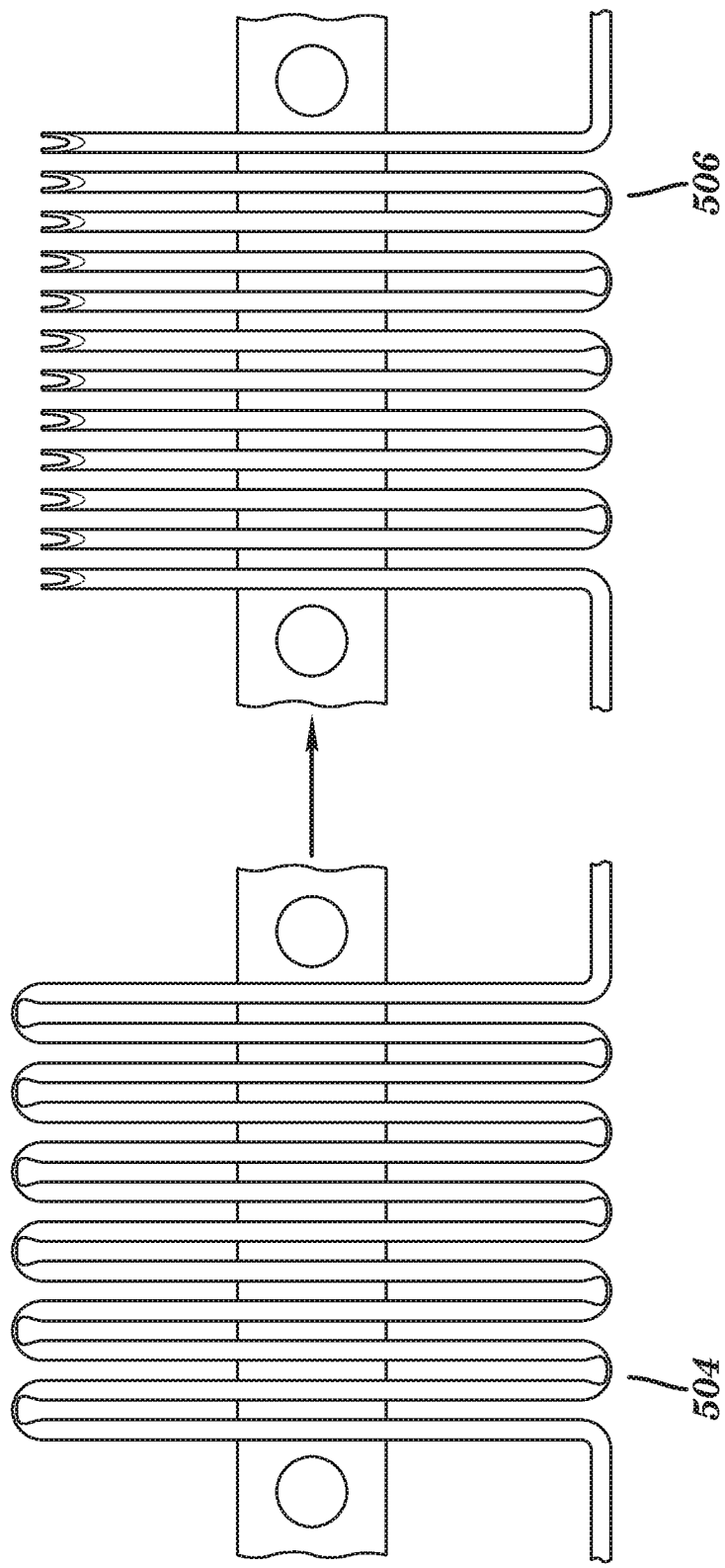
FIGS. 6A and 6B are photographs of arrays of needles at various stages of the pick and place accordion method for manufacturing of needles, according to aspects of the present disclosure.

In some embodiments, sub-arrays may be stacked or ganged to form larger arrays. Stacking may be done before or after processing of sub-arrays. As discussed above with respect to FIG. 2, a wide variety of geometric arrangements of neighboring layers are possible, including square lattice, triangular lattice, hexagonal lattice, etc. Any portion of the array may be bonded, encapsulated, or otherwise incorporated into a larger structure with the intention of imparting support, strength, orientation, or other properties to the whole. The same fixturing (as shown in FIG. 5B) and forming methods may be used to form wire arrays, which may be used in conjunction with the needle arrays, for example, as precisely matched ejector pins. Wire and tube arrays may be formed in separate steps or in the same step. If formed in the same step, the wire may be threaded through the tubing before forming. The combination of tubing and wire would then be processed together (bent, ground, etc.), with the possible advantage of eliminating a later-stage assembly step. FIGS. 6A and 6B are photographs of folding tubing in the carrier and processed needles, respectively. In some embodiments, this "accordion" method can also be done without bent accordions. For example, long straight sections of tubes can be placed and bonded on several carriers at once. Once these are formed, the sections apart can be cut apart (one carrier per section) and then sharpened.

Tissue Stabilization

In some embodiments, a tissue stabilizer is implemented to apply pressure and stabilize the tissue at the donor site during extraction. Applying pressure to the donor site, for example, with the tissue stabilizer may reduce the amount of force required for the needles or array to penetrate the donor site, and thereby may reduce trauma at the donor site. FIGS. 7A-D depict a grafting device having a tissue stabilizer and method of operation thereof in accordance with embodiments of the present disclosure. FIGS. 7A-D depicts a strap as a tissue stabilizer. However, in embodiments that do not have the strap, the grafting device can be stabilized with a plastic housing that is around the needle array. The plastic housing can be composed of hard or soft material, can be combined with a softer, flared material that contacts the skin, and can be shaped such that in the event of multiple harvests, the housing can be lined up with an outline left from prior harvests—to minimize the harvest region/area. The plastic housing pushes against the skin to stabilize the skin and hold it down before and during harvesting. The strap can be used to assist in holding the plastic housing against the skin. Accordingly, the device is stabilized by having the user apply the pressure and stability of the device on the tissue site, for example, an arm, leg or any other harvest site. In some embodiments, the device can sense the proper force on the leg before allowing the actuating of the needles.

Figure 7A:
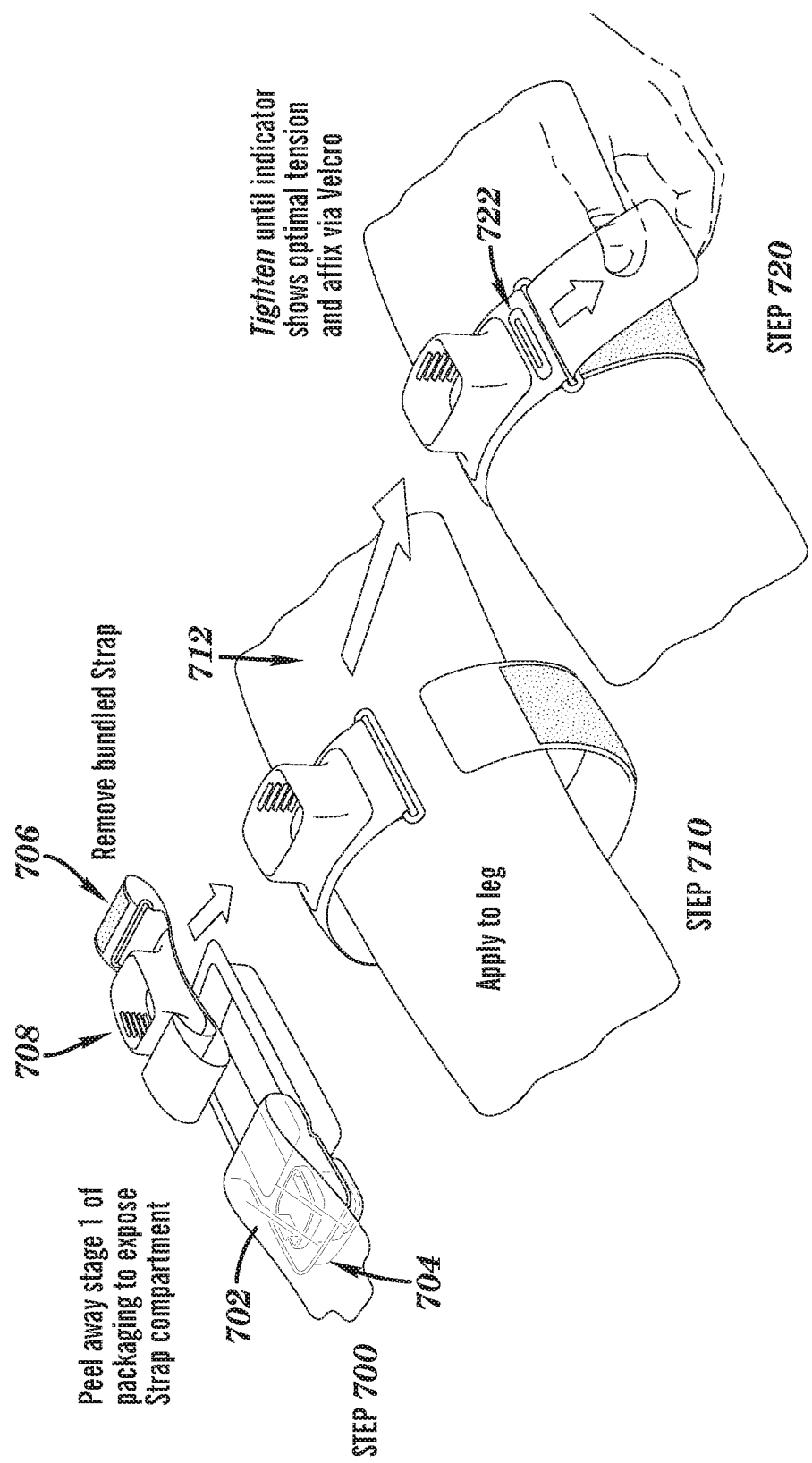
FIGS. 7A-D depict a grafting device including a tissue stabilizer and method of operation thereof in accordance with embodiments of the present disclosure.

FIG. 7A depicts at step 700, a disposable package 702 containing a disposable array 704 and a disposable strap 706 and a base 708. Disposable array 704 contains the needles for harvesting tissue from the donor site. At step 700, disposable strap 706 and base 708 are removed from disposable package 702. At step 710 disposable strap 706 and base 708 are applied to a patient, for example, to the patient's leg 712. At step 720, disposable strap can be tightened until an indicator 722 shows that an optimal tension has been obtained.

Figure 7B:
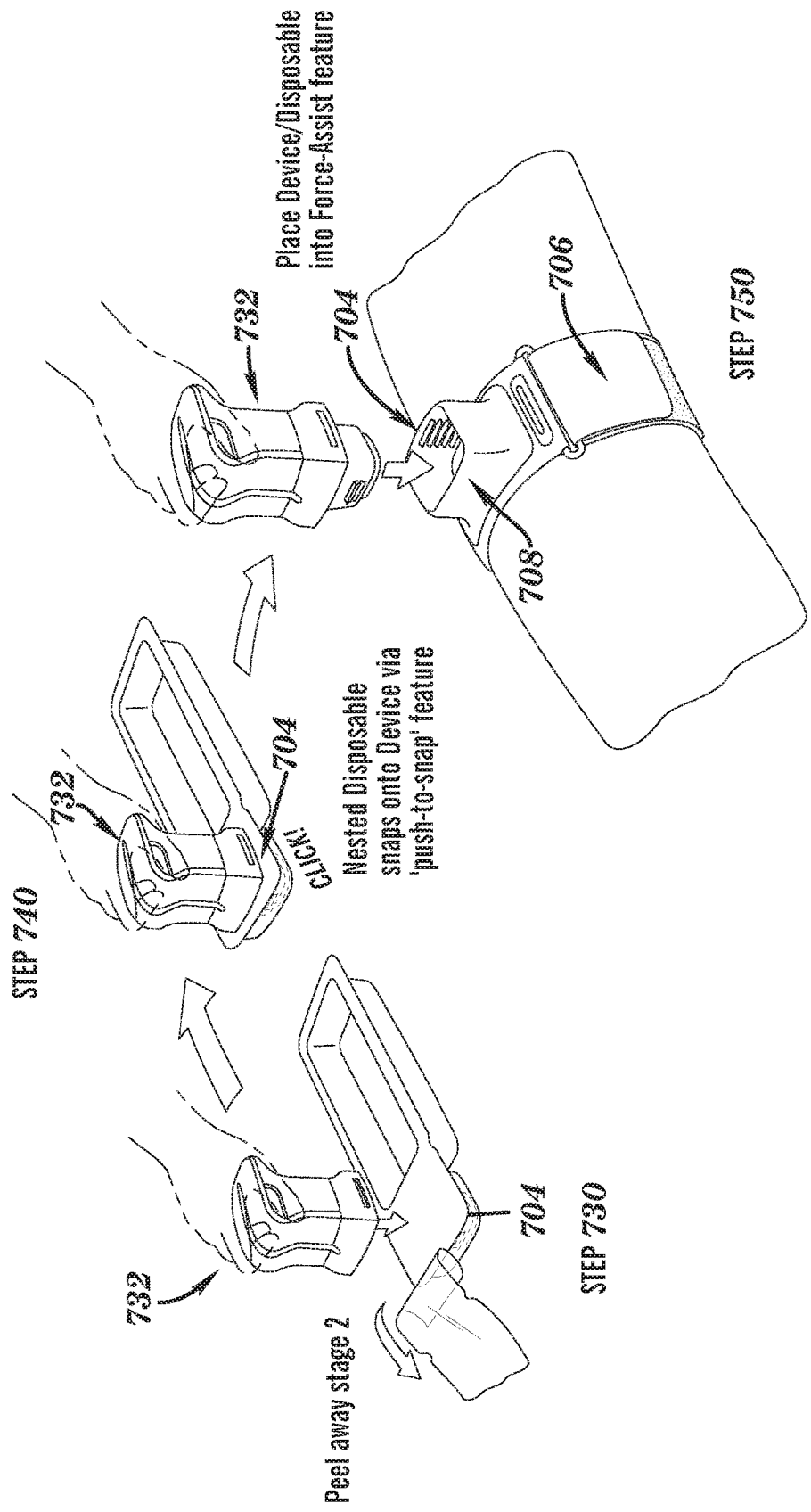

FIG. 7B depicts fully opening disposable package 702 to allow a device 732 to access disposable array 704. Step 740 shows device 732 clicking and locking into disposable array 704. Step 750 depicts device 732 and disposable array 704 being placed into disposable strap 706.

Figure 7C:
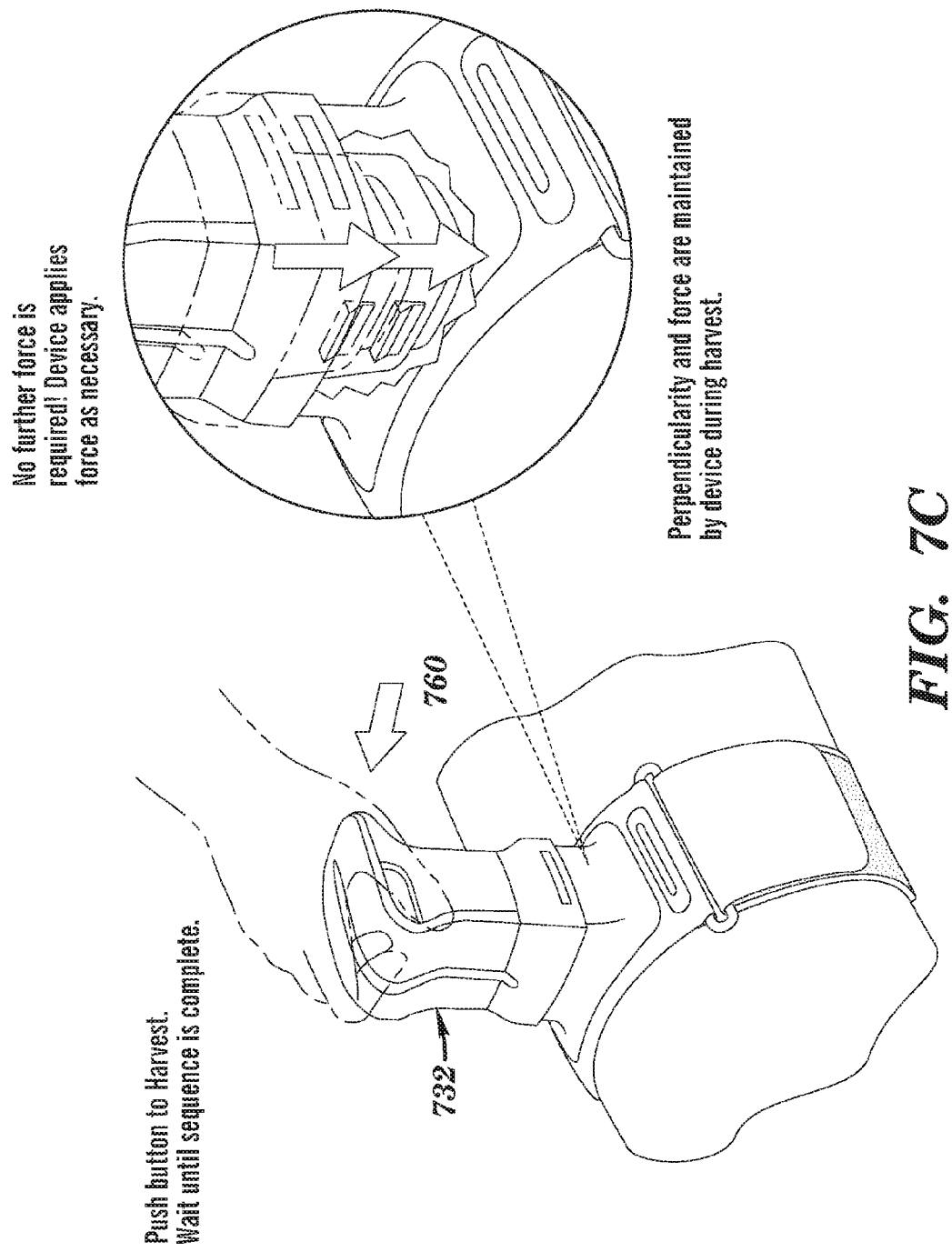
Figure 7D:
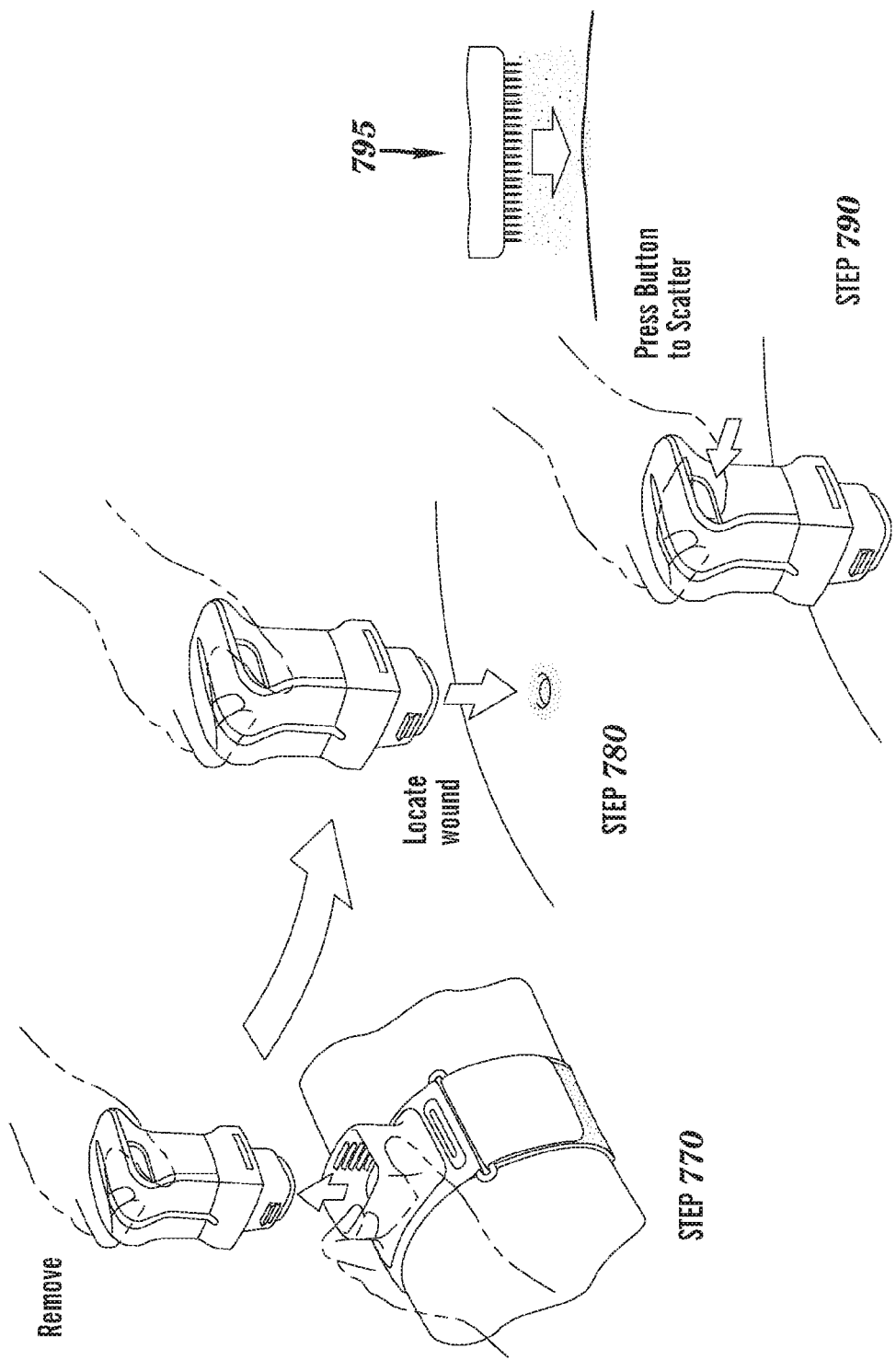

FIG. 7C depicts a tissue harvesting sequence. A button 760 is pressed by the user. Device 732 then maintains the appropriate force during harvesting without further input or force from the user. The user simply waits until the harvesting sequence is complete. FIG. 7D depicts removal of device (step 770), positioning of device with harvested tissue over a wound (step 780) and scattering of harvested tissue over wound (step 790). A user can press button 760 to scatter the harvested tissue from the needles onto the treatment site, as shown in more detail at 795.

While a strap has been shown in the above figures as the means for securing the device to the donor site, other means for securing the device also can be used. For example, in some embodiments, the device can be secured using an adhesive or a clamp. Further, in some embodiments, before insertion of needles into the donor site, the angle or perpendicularity of the device can be checked and adjusted to insure that the tissue is not harvested at an angle. For example, the device can be kept to within +/−10 degrees from vertical.

In some embodiments, the device can have a force sensor. The force sensor can detect the force with which the user is applying the device to the skin. Once the user has achieved what is considered an optimal force, the device notifies the user that the optimal force has been reached and that the user can begin deployment of the device. The device can use the force sensor to know that enough force has been applied prior to harvesting. Alternatively, if the user is applying the force (with our without a strap), the device will check to be sure the user is pushing hard enough to successfully penetrate the donor site before harvesting. In some embodiments, the optimal force can be in the range of about 10 to 40 lbs. The device also can measure and monitor force throughout the harvesting sequence and can alert the user if a proper force is applied and/or if the force applied drops below an acceptable level. The alert can be visual or audible.

In some embodiments, the strap can contain multiple ports for access to multiple harvesting sites. In these embodiments, a throw-away shield can be included in each port on the strap, which can attach itself to the cartridge after harvesting. The purpose of the throw away shield is to prevent contamination of the donor site when going back to harvest a second time if the cartridge comes in contact with the wound during scattering. The user can then dispose of the throw-away shield before harvesting again at a second port and again at additional ports. The throw away shield also prevents a user from going back into the same port twice, e.g., harvesting from the same area twice.

Vibration Assisted Coring

Figure 8A:
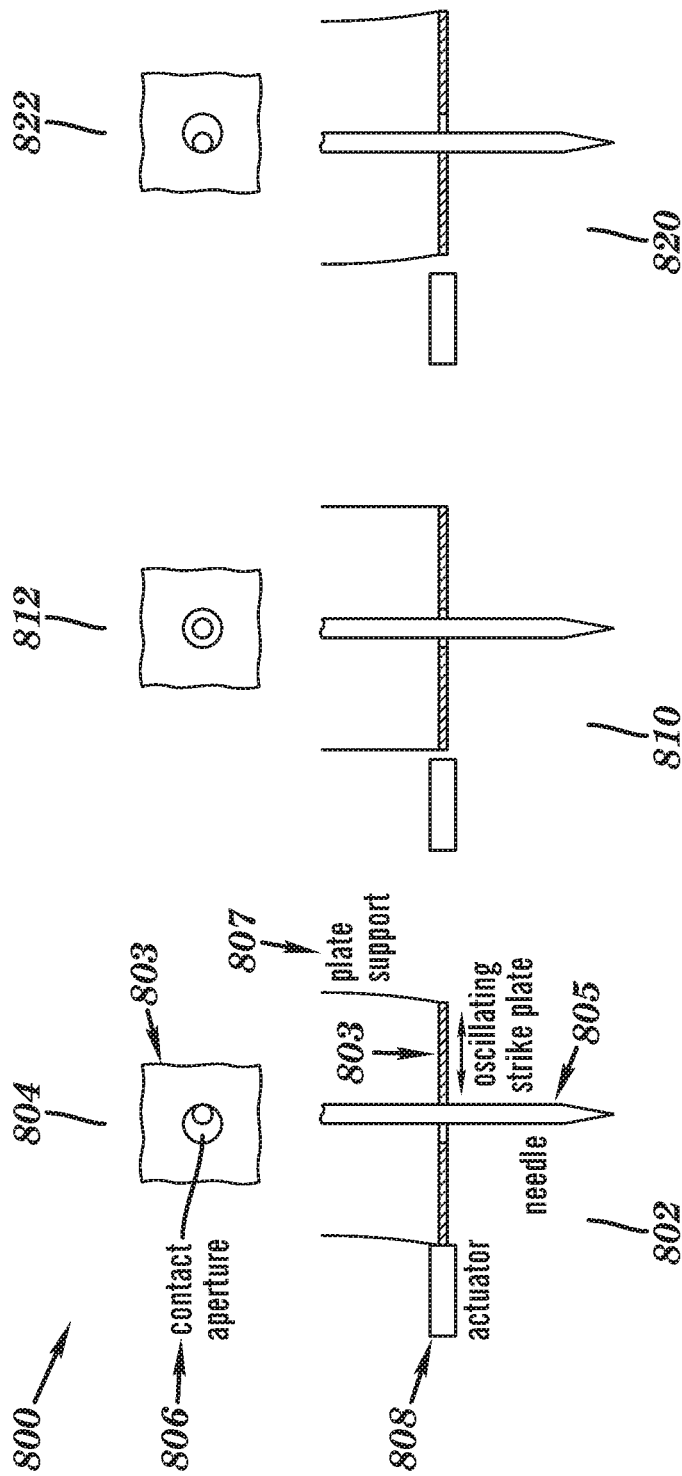

In some embodiments, vibrating the needles upon entry into the donor site can help reduce needle insertion forces and accordingly reduce damage to tissue and pain to the patient. FIG. 8A depicts an apparatus 800 for the vibratory actuation of a needle. FIG. 8A depicts three states of the same configuration, first state 802/804, second state 810/812, and third state 820/822. For each state, a top view (804, 812, 822) and a side-sectional view (802, 810, 820) are shown.

In some embodiments, apparatus 800 can include an oscillating strike plate 803 which surrounds a needle 805 by means of a contact aperture 806. Strike plate 803 can be supported by one or several plate supports 807, which permit and encourage the lateral or sideways motion of strike plate 803 such that it may strike needle 805 one or several times per oscillation. In some embodiments, strike plate 803 may be set into oscillatory motion, and its motion maintained, by any of several means, including but not limited to piezoelectric, electromechanical, pneumatic, fluidic, mechanical, or magnetostrictive actuators 808. One or more actuators 808 may be employed. The schematic is intentionally not drawn to scale; in practice, the amplitude of the vibration of strike plate 803 may be as small as several micrometers, but it may be considerably larger as well. In the first state 802/804, actuator 808 actuates oscillating strike place 803 and causes a side of needle 805 to come into contact with strike plate 803. In second state 810/812, strike plate 803 has moved away from actuator 808 and is centered around needle 805. In third state 820/822, strike plate 803 comes into contact with the opposite side of needle 805. In some embodiments, strike plate 803 can be composed or metal or plastic.

In this embodiment, strike plate 803 and needle 805 are independently mounted and mobilized. That is, needle 805 may be moved independently of strike plate 803. For example needle 805 may be translated vertically (up or down) through contact aperture 806, without any need to translate vertically strike plate 803 and its supports 807. Further, as shown in FIG. 8A, the energy of actuator 808 is directed into strike plate 803 rather than directly into needle 805. This permits the design and selection of specific vibratory properties for strike plate 803 assembly, such as resonant frequency, independent of the needle actuation schemes.

Figure 8B:
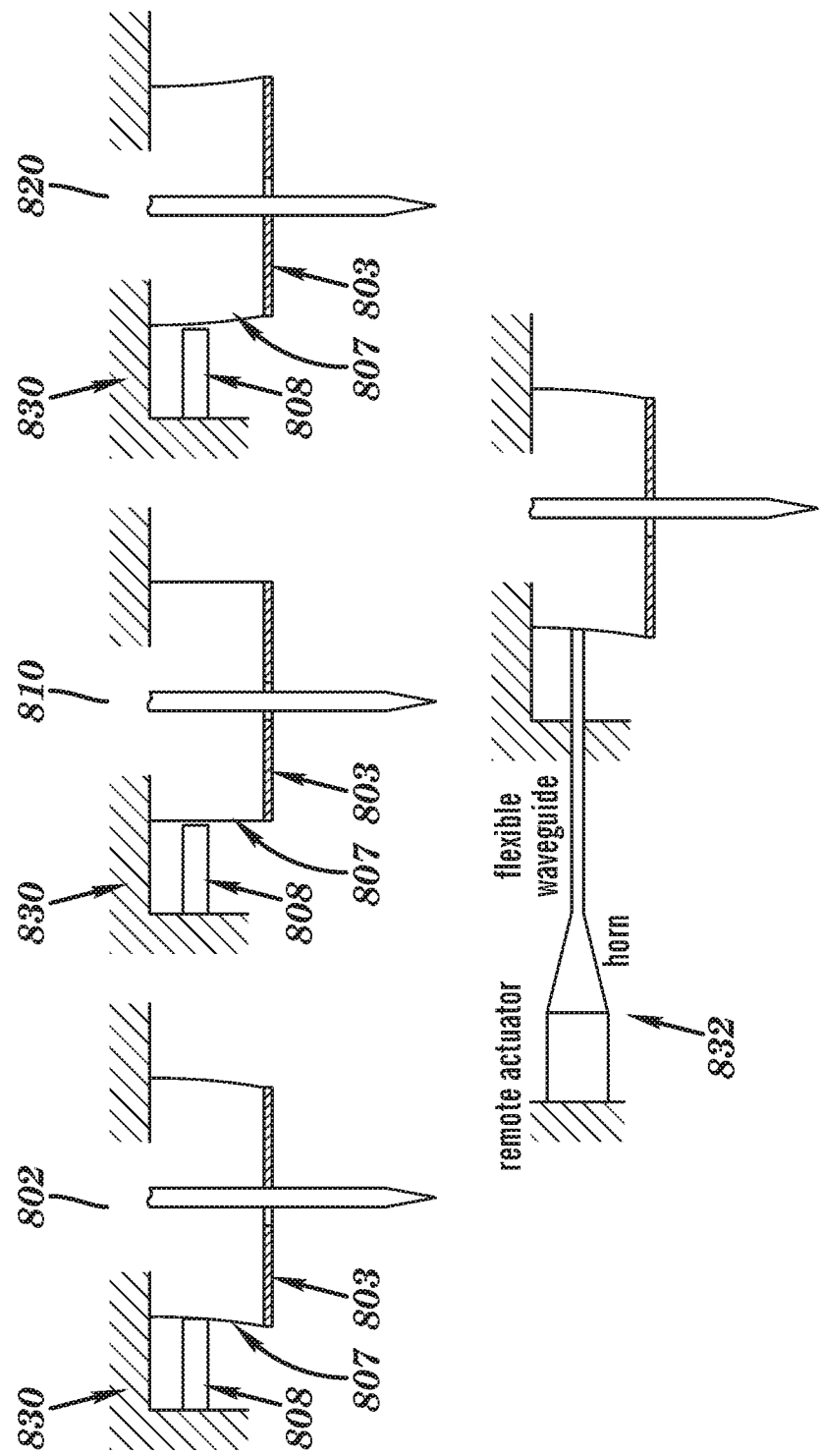

Five general methods of coupling the actuator to the strike plate are shown in FIGS. 8B-8F. It will be understood that a single actuator and a single needle are shown for illustrative purposes, but that the schemes may be extended to include several actuators and several needles, as shown in FIG. 8G. FIG. 8B depicts vibratory actuation system in first state 802, second state 810 and third state 820, actuator 808 secured to a stationary base 830 and is loosely coupled to the strike plate 803 or its support structure 807. The free-end of the actuator intermittently contacts the strike plate (or a portion of its supporting structure). The resonant properties of the strike plate and its supporting structure are independent of the actuator. The contact point of the actuator may be such as to effect amplification of displacement. For example, in FIG. 8B, the actuator makes contact at an intermediate point between the node and anti-node of vibration of the plate support. The motion of the strike plate may be such as to contact the needle once per oscillation, twice per oscillation (as shown in the FIG. 8B), or multiple times per oscillation. The energy of the actuator may be conveyed to the point of contact via a waveguide 832 or similar transmission element, which may also include displacement amplification, as shown in the second figure below.

Figure 8C:
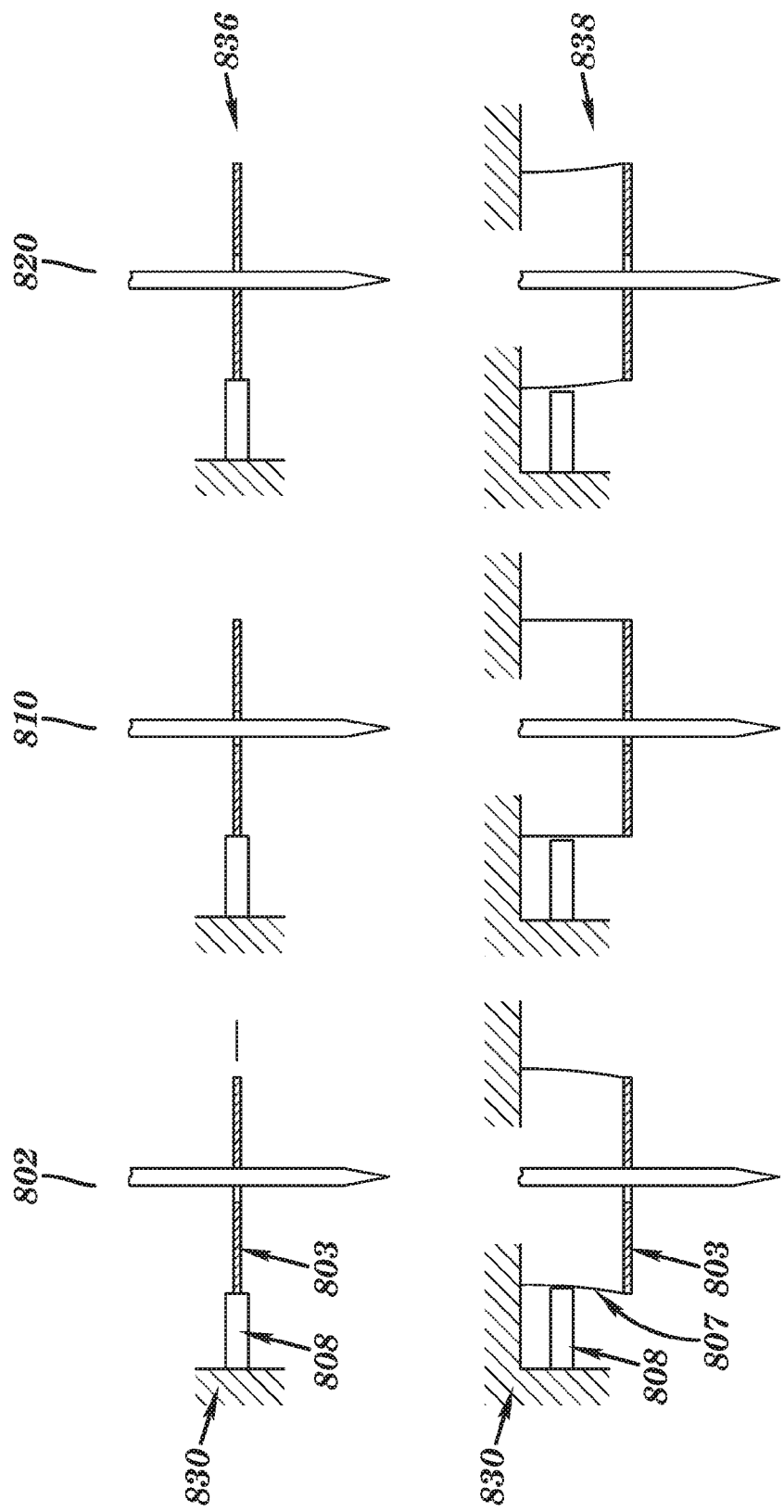

FIG. 8C depicts vibratory actuation system in first state 802, second state 810 and third state 820, in an arrangement where actuator 808 is secured to a stationary base 830 and is tightly coupled to strike plate 803 (shown at top row 836) or its support structure 807 (shown at bottom row 838). The actuator (or a waveguide extension of the actuator) is attached to the strike plate 803 or to the strike plate support structure. Non-resonant vibrational modes may be excited with greater control than with the loosely-coupled scheme. The actuator may be simultaneously employed as a sensor, and as a result, vibrational feedback control becomes possible. In FIG. 8C, while the actuator is attached to the strike plate, it does not travel with the strike plate. In some embodiments, it is also attached to a fixture that is substantially heavier than the strike plate (the device handle, for example), so that this other fixture is essentially "stationary." This way, the strike plate only moves exactly the way the actuator is moving it the frequency and amplitude of oscillation can be controlled.

Figure 8D:
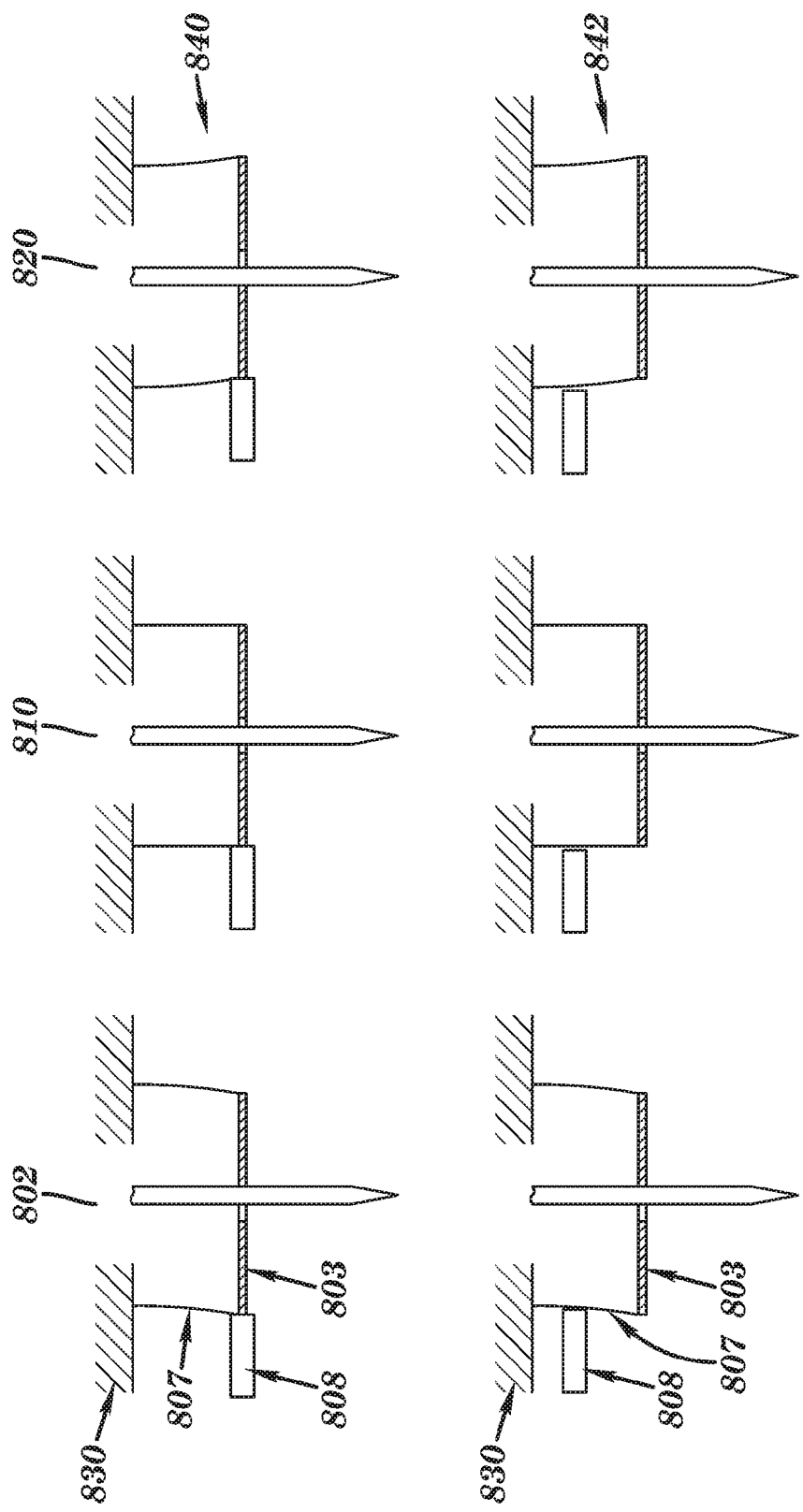

FIG. 8D depicts vibratory actuation system in first state 802, second state 810 and third state 820, in an arrangement where actuator 808 is tightly coupled to the strike plate 803 (shown in top row 840) or its support structure (shown in bottom row 842), and actuator 808 travels with strike plate 803. In this embodiment, very low mass schemes are possible and complex modes of vibration are typical. In some embodiments, a lower mass scheme refers to the actuator not being attached to something substantially heavier to stabilize it. In this scheme, the actuator is attached only to the strike plate. Complex modes of vibration refer to modes more complex than a simple wave pattern because the strike plate and actuator move together, so complex modes would occur as multiple waves interacted with each other.

Figure 8E:
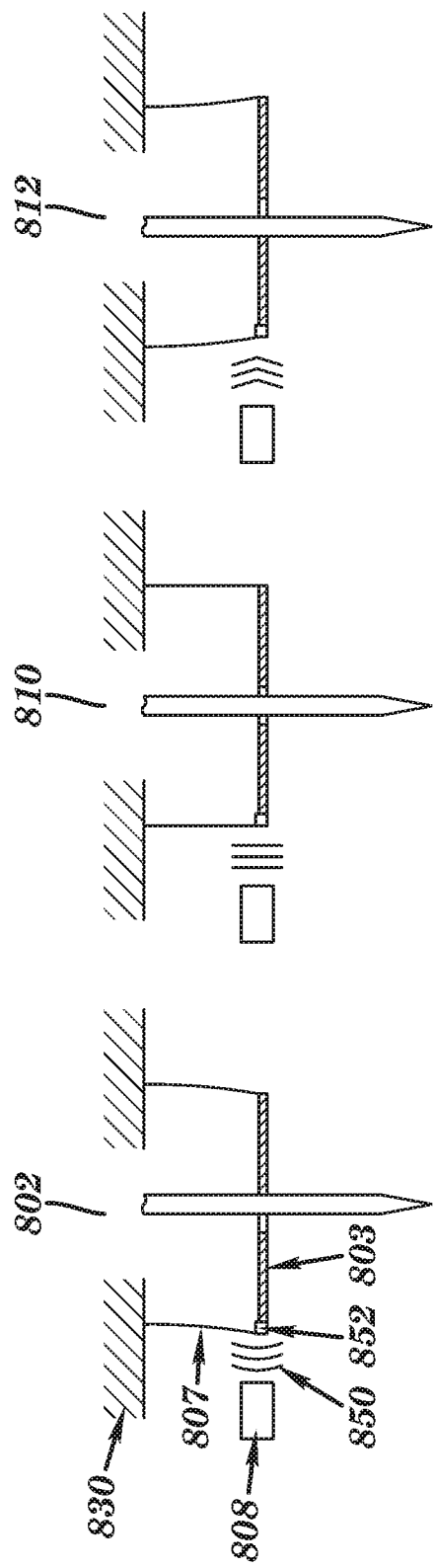

FIG. 8E depicts vibratory actuation system in first state 802, second state 810 and third state 820, in an arrangement where actuator 808 is as secured to a stationary base 830 and is energetically coupled 850 to the strike plate 803 or its support structure 807 through transducer 852 without physical contact. Any of several means of energy transfer are possible, including inductive, electrostatic, acoustic, and pneumatic. Depending on the technology used, transducer 852 could be piezo, EMF, magneto, mechanical, or another type of transducer.

Figure 8F:
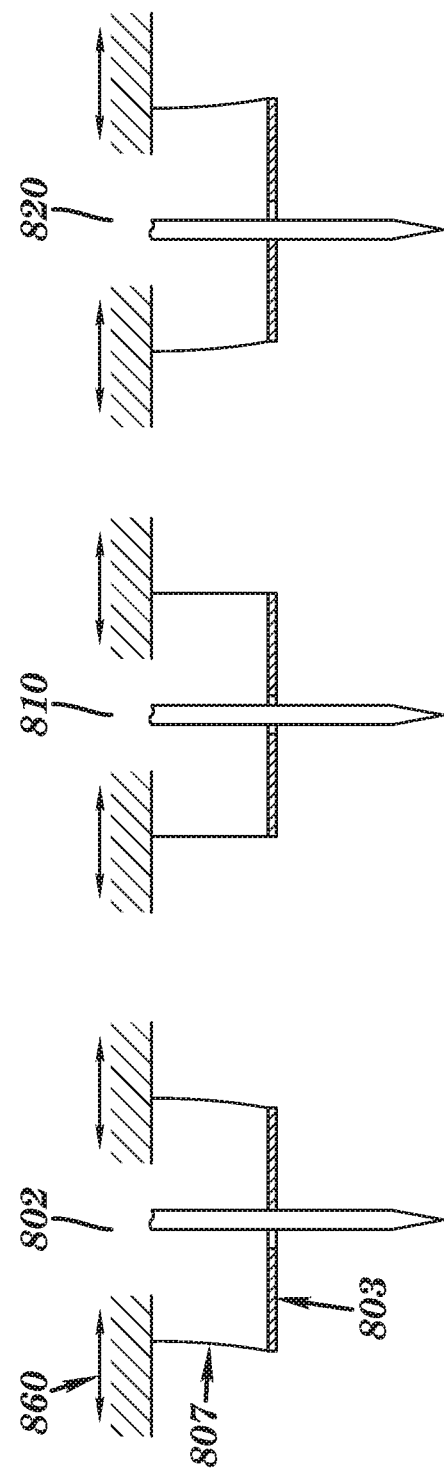
Figure 8G:
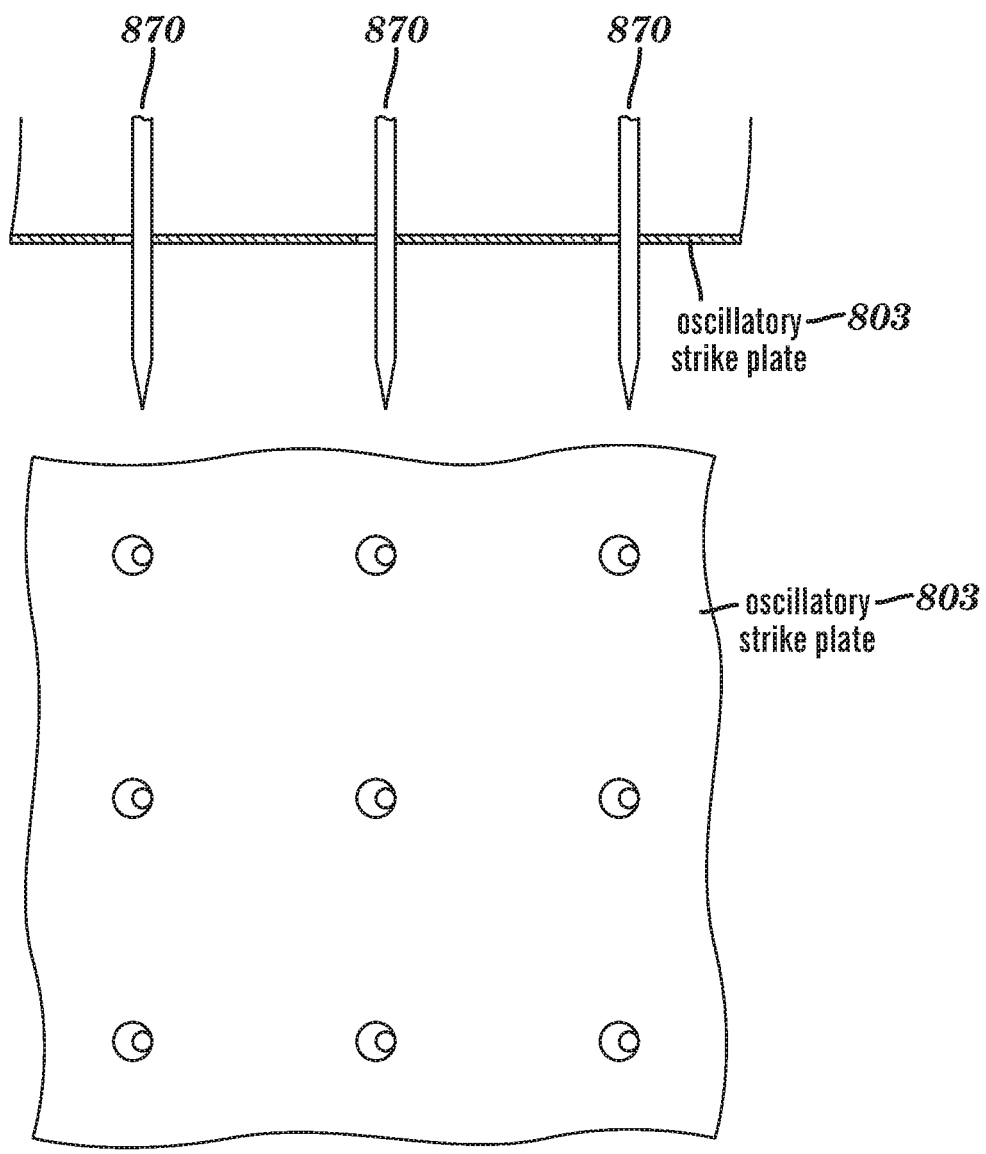

FIG. 8F depicts vibratory actuation system in first state 802, second state 810 and third state 820, in an arrangement where actuation is effected indirectly, as a consequence of the general vibration of the assembly 860. The strike plate 803 and associated structure 807 is designed to vibrate harmonically when the overall assembly is jarred, for example, by the action of a solenoid elsewhere within the assembly, or by the action of a spring and ratchet mechanism elsewhere within the assembly. In some embodiments, vibration of the strike plate 803 may be synchronized with other actions or operations of the assembly. In some embodiments, vibration of the strike plate 803 may be triggered manually or automatically.

Operational Modes and Configuration

For any of the above described schemes, vibrational modes may be selected to be resonant or off-resonant. In some embodiments, vibration may be effected in conjunction with other operations. For example, vibration may be applied intermittently and briefly, as required, in conjunction with an impulse energy source, such as a solenoid, that may be applied directly to the needle. In some embodiments, feedback control (for those instances where the actuator is simultaneously used as a sensor), may be used to control the duration and timing of vibrational actuation. Further, frequency and displacement amplitude may be selected over a very wide range: sub-sonic, sonic, and ultrasonic.

Vibration assistance may be effected for needle advancement, retraction, or ejection of cored material. In some embodiments, the contact aperture of the strike plate may be shaped to effect one contact per oscillation or several contacts. The roughness and/or sharpness of the aperture may be configured to influence the quality of the resulting vibration of the needle. Further, in some embodiments, the position of contact between the strike plate and the needle may be selected to influence the amplitude and mode of vibration of the needle.

In some embodiments, the strike plate and its associated structural components may be designed to oscillate as a result of direct or indirect actuation, and actuation may be effected manually or automatically (electronically). Direct actuation includes, but is not limited to, vibratory sources such as piezoelectric elements, magnetostrictive elements, electromagnetic solenoids, mechanical springs and ratchets, pneumatic bursts, fluidic oscillations, acoustic energy, etc. Indirect actuation includes any jarring motion of the entire assembly that might be effected by means, for example, of a solenoid action. Thus, the advancement or retraction of the needles by means of some mechanical action may be used to simultaneously induce a vibrational oscillation of the strike plate, which would then impart vibration to the needle. Direct actuation schemes include methods of physical contact as well as methods of non-contact. For example, the actuator may be positioned remotely from the strike plate, and the vibrational energy of the actuator may be conveyed to the strike plate or to its structural components by direct contact with flexible waveguides, or without contact via electromagnetic induction, magnetostrictive induction, or acoustically through the air.

FIG. 8G depicts the use of an oscillatory strike plate 803 to a needle array 870, according to some aspects of the present disclosure. The strike plate 803 may be configured to impinge upon a 1D or 2D array of needles 870. Any single needle or multiple needles may be moved into or out of the contact apertures at any time.

Modes of Oscillation

FIG. 8H depicts two modes of operation of the vibratory actuation system. Depending upon several parameters (the number, positions, and sequencing of actuator elements, the shape and mass of the strike plate 803, the stiffness and orientation of the flexible supports, etc.), the strike plate 803 may be oscillated over a wide range of motions, including simple linear (shown at left 880) to a phased quasi-circular motion (shown at right 890). Linear mode 880 contains one actuator 808 that moves in a single linear plane, shown as A⇌B. Phased quasi-circular mode 890 can have three actuators 808, where each actuator can move in separate planes A, B, and C. The vibration in FIG. 8H is perpendicular to the axis of the needles; however, it does not need to be. The vibration could be applied in any direction, including in the axis of the needles. One way to vibrate along the axis of the needles can be to send very short and quick signals to the solenoid, thereby "chattering" it.

Stem Cells/Fat Tissue

The described micrografts can include skin tissue that can include, e.g., epidermal and dermal tissue, and/or tissue obtained from other body organs. The micrografts can have at least one dimension that is relatively small, e.g., less than about 1 mm, or less than about 0.5 mm, or optionally about 0.3 mm or less, or about 0.2 mm. Such exemplary small dimensions of the micrografts can facilitate both healing of the donor site following harvesting, and viability of the micrografts by allowing greater diffusional nourishment of the micrograft tissue. The small regions of damage in the donor site caused by a removal of the tissue portions can heal rapidly with little or no formation of visible scars. The micrografts obtained from skin tissue can include, e.g., epidermal and dermal tissue, and can also include stem cells that can be located proximal to the dermal/fatty layer boundary.

An exemplary micrograft can have an elongated shape that may be approximately cylindrical. The micrografts can include both epidermal tissue and dermal tissue from the exemplary donor site. For example, the exemplary micrograft can be about 3 mm length, which can correspond to a typical total depth of the skin layer (e.g., epidermal and dermal layers). A different length may be used based on the particular skin or tissue characteristics of the donor site. In prior applications, it has be noted that it can be preferable to avoid harvesting a significant amount of subcutaneous tissue, so the harvested micrografts can include primarily the epidermal tissue and the dermal tissue. For example, prior art techniques for performing skin grafts remove or scrape off any adipose or fatty tissue from a skin graft before applying the graft to a wound site. This has been done because the fatty tissue is generally seen as a by-product of the harvesting process that adversely interferes with the ability of the grafted skin to access the blood supply at the wound site. Therefore, in prior methods, all fatty tissue is cleaved from the graft.

However, according to aspects of the present disclosure, because of the small size of the micrograph columns, these columns generally can survive at the wound location via diffusion without having to form a good connection to the blood supply at the wound location. Accordingly, it may be helpful to include subcutaneous tissue in the micrograft, as adipose tissue in the subcutaneous tissue contains stem cells. Thus, if the depth of the micrograft can extend to a lower portion of the dermal layer of the donor site (e.g., near a dermal/fatty layer boundary) and even into the dermal/fatty layer boundary, the micrografts can include stem cells, for example, mesenchymal stem cells. These stem cells can facilitate healing and integration of the exemplary micrografts when they are scattered or inserted into a recipient site.

Additionally, prior art methods of harvesting adipose-derived stem cells have required isolating and purifying the stem cells from the adipose tissue. See e.g., U.S. Pat. No. 6,777,231 to Katz. However, according to aspects of the present disclosure, the healing benefits of the stems cells can be realized without processing, isolation or purification of the stem cells. The presence of the stem cells within the fatty tissue of the micrograft alone can result in increased healing and integration of the micrograft. Accordingly, it may be beneficial in include at least 5% or 10% of fatty, adipose tissue in the micrografts to realize the benefits of the stems cells at the recipient site. Therefore, according to some embodiments of the present disclosure, the micrografts can be up to 4 or 5 mm in length to access the adipose cells in the fatty tissue layer.

Rotation and Actuation of Needles

In some embodiments, individual needles can be rotated. This can be effected by rotating the full array of needles through the use of gears or o-rings, or any other means of rotation. The rotation of the needles upon entry of the needles to the donor site allows for low force coring of the skin. In some embodiments, the use of rotation allows for the better use of straight cut, sharpened edges of the needles.

In some embodiments, the needles can be driven into the donor site using an electric hammer. This electric hammer can have a rotating cam that hits a plunger to move the needles multiple times per second. In this embodiment, the use of the automatic hammer can drive the needles into the donor site more gradually than the solenoid actuation.

In further exemplary embodiments of the present disclosure, the exemplary methods and apparati described herein can be applied to other tissues besides skin tissue, e.g., internal organs such as a liver or heart, and the like. Thus, grafts can be formed for a variety of tissues while producing little damage to a donor site and facilitating rapid healing thereof, while creating graft tissue suitable for placement at recipient sites.

The subject matter described herein can be implemented alone or in conjunction with a system that facilitates removal of tissue from a donor site, and/or scatters or otherwise disposes tissue at a recipient site or other site. It is to be understood that the disclosed subject matter is not limited in its application to the details of construction and to the arrangements of the components set forth in the preceding description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the concept, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method for harvesting biological tissue, the method comprising:
   providing a device having a plurality of segments of hollow tubes, each hollow tube comprising at least one point at the distal end of the hollow tube, the plurality of segments forming a two dimensional array of hollow tubes, wherein each segment comprises a plurality of hollow tubes;
   positioning the two dimensional array of hollow tubes proximal to an upper surface of a biological tissue;
   advancing simultaneously with a single actuator only the plurality of hollow tubes of a first segment of the two dimensional array of hollow tubes into the biological tissue to sever portions of the biological tissue from the surrounding tissue wherein the first segment comprises a row of hollow tubes, a plurality of rows of hollow tubes, a portion of a row of hollow tubes, or a plurality of portions of rows of hollow tubes;
   subsequently advancing simultaneously with the single actuator only the plurality of hollow tubes of a second segment of the two dimensional array of hollow tubes into the biological tissue to sever portions of the biological tissue from the surrounding tissue wherein the second segment comprises a row of hollow tubes, a plurality of rows of hollow tubes, a portion of a row of hollow tubes, or a plurality of portions of rows of hollow tubes; and
   raising the two dimensional array of hollow tubes from the position proximal to the upper surface of the biological tissue such that the biological tissue remains in each of the hollow tubes of the first and second segments.

2. The method of claim 1, wherein each hollow tube has an inner diameter less than about 1 mm.

3. The method of claim 1, wherein each hollow tube has an inner diameter less than about 0.8 mm.

4. The method of claim 1 comprising: providing a plurality of pins, each of the pins located within a central lumen of each of the hollow tubes.

5. The method of claim 4, comprising:
   positioning the two dimensional array of hollow tubes over a wound site;
   scattering the biological tissue within each of the hollow tubes of the first segment over the wound; and
   scattering the biological tissue within each of the hollow tubes of the second segment over the wound.

6. The method of claim 5, wherein the scattering of the first segment and the second segment occur at the same time.

7. The method of claim 5, wherein the scattering of the first segment and the second segment occur at different times.

8. The method of claim 5, wherein the biological tissue comprises skin tissue and adipose tissue.

9. The method of claim 1, wherein the raising of the first and second segments occur at the same time.

10. The method of claim 1, wherein the raising of the first and second segments occur at different times.

11. The method of claim 1, wherein advancing comprises firing a solenoid.

12. The method of claim 1, wherein the two dimensional array comprises a circle.

13. The method of claim 12, wherein the circle comprises an area of about one square inch.

14. The method of claim 1, comprising about 300 hollow tubes.

* * * * *